(12) United States Patent
Lootens et al.

(10) Patent No.: US 8,215,172 B2
(45) Date of Patent: Jul. 10, 2012

(54) DEVICE AND METHOD FOR DETERMINING THE DYNAMIC ELASTIC MODULUS OF A MATERIAL

(75) Inventors: Didier Lootens, Zurich (CH); Julien Lopez Rios, Zurich (CH); Robert Flatt, Zurich (CH); Norman Blank, Zurich (CH)

(73) Assignee: Sika Technology AG, Baar (CH)

( * ) Notice: Subject to any disclaimer, the term of this patent is extended or adjusted under 35 U.S.C. 154(b) by 747 days.

(21) Appl. No.: 11/886,563

(22) PCT Filed: Apr. 20, 2006

(86) PCT No.: PCT/EP2006/061705
§ 371 (c)(1),
(2), (4) Date: Jan. 26, 2009

(87) PCT Pub. No.: WO2006/111559
PCT Pub. Date: Oct. 26, 2006

(65) Prior Publication Data
US 2009/0205427 A1 Aug. 20, 2009

(30) Foreign Application Priority Data
Apr. 20, 2005 (EP) .................................. 05103192

(51) Int. Cl.
*G01N 29/11* (2006.01)
(52) U.S. Cl. .......................................... 73/596; 73/602
(58) Field of Classification Search .................... 73/596, 73/597, 602
See application file for complete search history.

(56) References Cited

U.S. PATENT DOCUMENTS

| | | | |
|---|---|---|---|
| 3,303,694 A | 2/1967 | D'Onofrio | |
| 4,754,645 A | 7/1988 | Piche et al. | |
| 5,040,419 A * | 8/1991 | Allaire et al. | 73/597 |
| 5,170,667 A * | 12/1992 | Takeuchi et al. | 73/597 |
| 5,412,990 A | 5/1995 | D'Angelo et al. | |
| 5,433,112 A * | 7/1995 | Piche et al. | 73/597 |
| 5,741,971 A * | 4/1998 | Lacy | 73/597 |
| 5,847,267 A * | 12/1998 | Janzen | 73/54.01 |
| 5,992,223 A * | 11/1999 | Sabins et al. | 73/64.42 |
| 6,164,818 A * | 12/2000 | Dick et al. | 374/46 |
| 6,655,213 B1 | 12/2003 | Reinhardt et al. | |
| 6,941,819 B1 * | 9/2005 | Maki et al. | 73/803 |
| 7,856,881 B2 * | 12/2010 | Coghill | 73/597 |
| 2007/0157698 A1 * | 7/2007 | Allaire et al. | 73/12.01 |
| 2009/0078046 A1 * | 3/2009 | Coghill | 73/597 |

OTHER PUBLICATIONS

B. Coluzzi et al.; "Computer-controlled apparatus for internal friction and Young's modulus measurements as a function of temperature;" *Rev. Sci. Instrum.*; vol. 67, No. 12; Dec. 1996; pp. 4240-4245.
Christian U. Grosse et al.; "Continuous Ultrasound Measurements During Setting and Hardening of Concrete;" *Otto Graf Journal*; vol. 5, 1994; pp. 76-98.
Zhonghui Li et al.; "Design Considerations for High Sensitivity Guided SH-SAW Chemical Sensor for Detection in Aqueous Environments;" 2004 IEEE International Ultrasonics, Ferroelectrics, and Frequency Control Joint 50th Anniversary Conference; pp. 185-192.

* cited by examiner

*Primary Examiner* — J M Saint Surin
(74) *Attorney, Agent, or Firm* — Oliff & Berridge, PLC

(57) ABSTRACT

The invention relates to the determination of the dynamic elastic modulus of a material, such as a material comprising a mineral binder like cement, or gypsum, or the like, or a polymer, or ceramic, preferably mortar or concrete, in particular shotcrete, using sound, preferably ultrasound waves which penetrate the material and are continuously measured and analyzed. In particular, the invention relates to an apparatus, to a measuring device, and to a method for determining the dynamic elastic modulus of a material using the apparatus.

28 Claims, 11 Drawing Sheets

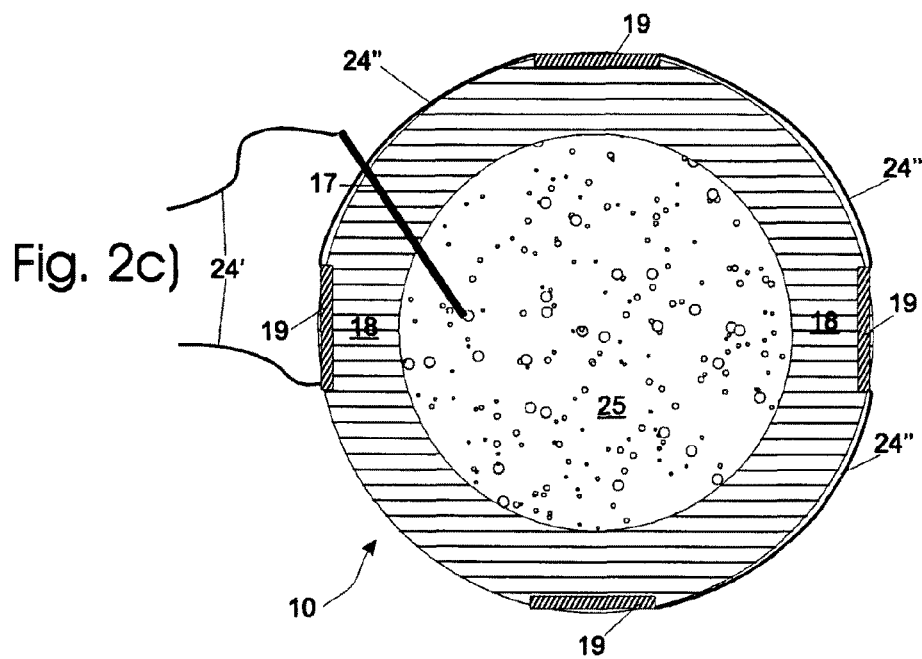
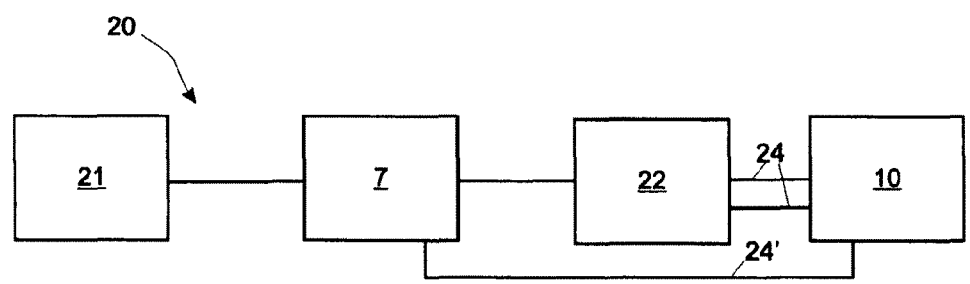

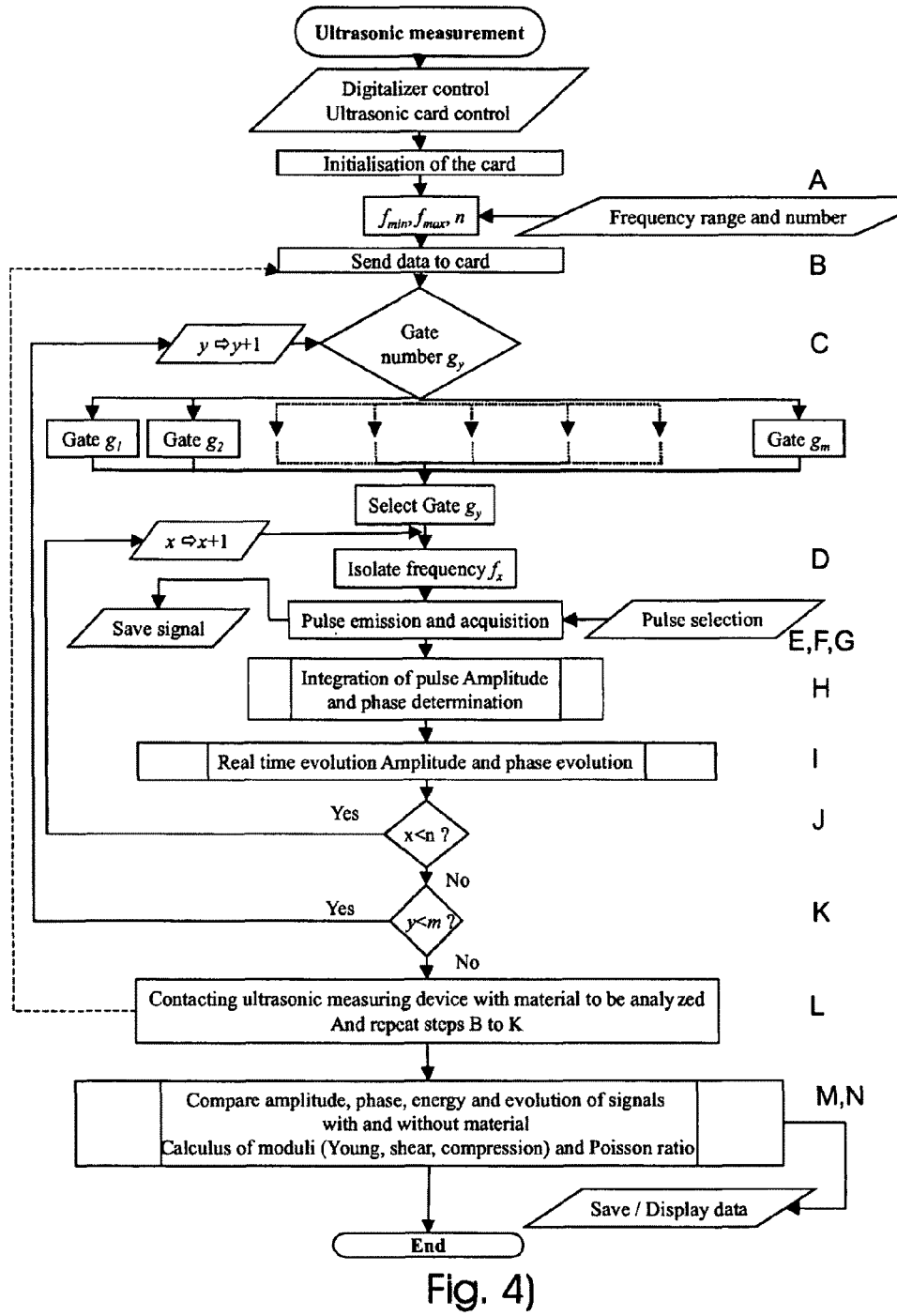
Fig. 4)

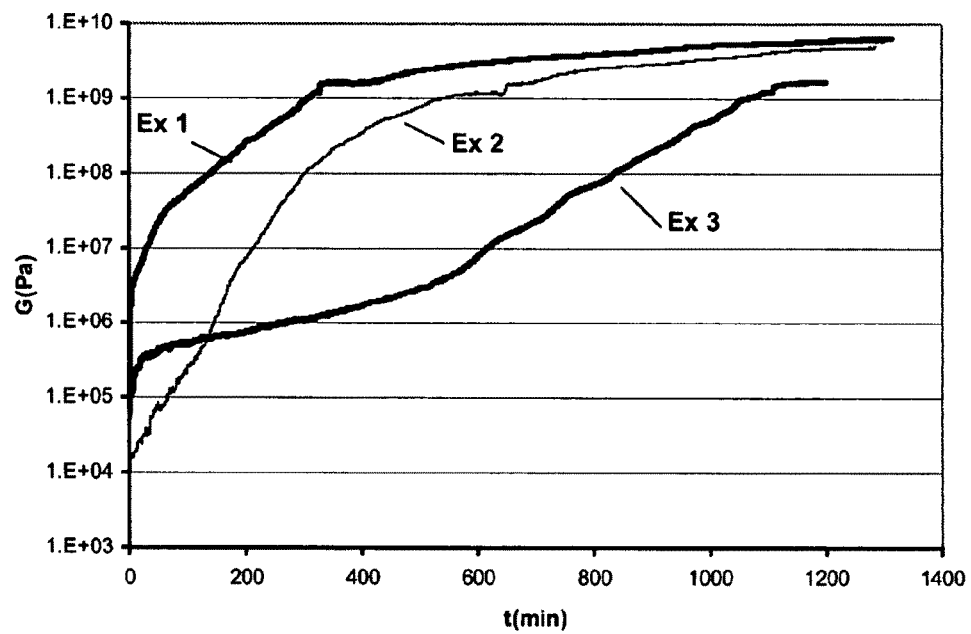
Fig. 6)
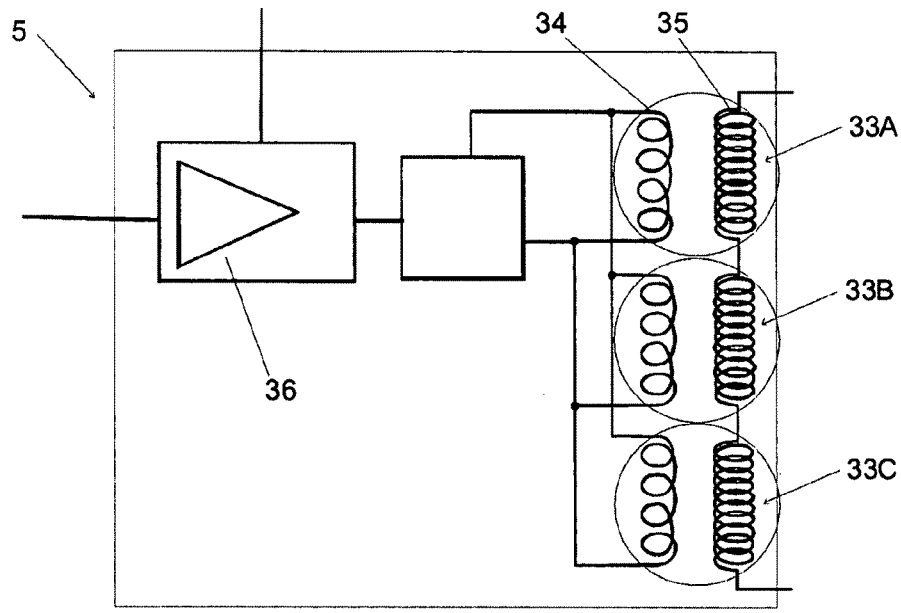
Fig. 7)

DEVICE AND METHOD FOR DETERMINING THE DYNAMIC ELASTIC MODULUS OF A MATERIAL

TECHNICAL FIELD

The invention relates to the determination of the dynamic elastic modulus of a material, such as a material comprising a polymer, or ceramic, or a mineral binder like cement or gypsum, or the like, in particular a material such as mortar, concrete, in particular shotcrete, using sound waves, preferably ultrasound waves, which penetrate the material and are continuously measured and analyzed. In particular, the invention relates to an apparatus, to a measuring device, and to a method for determining the dynamic elastic modulus of a material using the apparatus.

BACKGROUND OF THE INVENTION

Classical tools for measuring material properties of a material comprising mineral binders and polymers are for example the Vicat test, penetrometer, rheometer, needle penetration, or compression testing equipment like e.g. from Instron®. These tools, however, cannot be used for monitoring the complete time evolution of the chosen material properties.

Ultrasonic analysis methods for measuring material properties of mineral binders are known. U.S. Pat. No. 5,412,990 discloses a method and apparatus for determining the setting time of a cement slurry using acoustic shear wave signals. U.S. Pat. No. 6,655,213 discloses a method for examining a solidifying and/or hardening material using ultrasound waves.

Existing ultrasound devices used for the characterization of rheological and mechanical properties of a material operate over a narrow range of high frequencies. This approach is satisfactory for homogeneous elastic materials only. In materials with air bubbles, porosity, cracks and/or inclusions that have a different ultrasonic response than the matrix, the material response can be more complex. In particular, it is often not possible to obtain true fundamental material properties without specific calibration.

The main disadvantage of the known devices is that they can only be used over a narrow range of frequencies, whereas dynamic elastic properties of a material can strongly depend on the excitative frequency. In addition, the devices known in the art are heavy and cumbersome, have high energy consumption and are therefore not suitable for easy on site measurement. Furthermore, existing devices do not offer direct display of material properties and rely on data processing subsequently to the measurement which is time consuming. Furthermore, existing devices have a high signal to noise ratio. Thus, there is a growing need for a non-destructive technique that can follow the direct time evolution of the dynamic elastic modulus of a material and for an apparatus that offers a high degree of portability and user friendliness.

SUMMARY OF THE INVENTION

Accordingly, one object of the invention is to provide an apparatus and reliable use of a test method in industry and to permit easy, continuous, non-destructive and non-invasive monitoring of the dynamic elastic modulus of a material such as a mineral binder or a polymer, and in particular to quantify the rheological and mechanical evolution of a material comprising a mineral binder such as cement, such as concrete, in particular shotcrete, or the like, from early age to far beyond the setting of a mineral binder, and in particular to provide a short response time from measurement to the displayed material property, which allows analysis of quickly hardening material, e.g. shotcrete applications. Thus, it is an object of the invention to provide an apparatus and device which has an improved signal/noise ratio compared to existing devices and which allows the characterization of a material by sound propagation methodology to be done over a broad range of frequencies, including frequency ranges from infrasound waves to ultrasound waves. This contrasts with existing ultrasound devices and is important for all viscoelastic materials as well as for materials containing inclusions such as air bubble, aggregates and porosity.

A further object of the invention is a method and a device for the direct and complete processing of the measured signals to display the determined material properties in real time.

In addition, it is a purpose of the present invention to provide a compact, portable apparatus for on site measurement which has low power consumption.

According to the invention, this is achieved by the features of the independent claims. Further advantageous embodiments of the invention emerge from the subclaims.

The apparatus, device, and method of the invention can be used for determining the dynamic elastic modulus for mineral binders as well as for polymers, in particular reactive polymers or oligomers, as well as for their cured products. In particular, the method is especially suitable to monitor the curing in real time. The apparatus, device, and method of the invention can also be used as a tool to control the quality of raw material, intermediate and final product. It may be used as a quality control or process control tool.

The present invention provides an apparatus for determining the dynamic elastic modulus of a sample of a material by means of sound waves, comprising (a) a measuring device with means for acoustically coupling the sample of the material to at least one transducer, which is coupled, preferably through a cable connection, to (b) a card comprising (i) means for receiving and processing response signals received from the transducer and (ii) means for generating signals of a high voltage over a wide frequency range, said means including a low-voltage frequency-adjustable electronic oscillator, a signal generator, an electronic switch, a high voltage wide-band amplifier, and optionally an electronic memory, wherein said high voltage wide-band amplifier comprises or is connected to at least one coreless transformer having primary and secondary windings, wherein said secondary windings are connected to the at least one transducer. In a preferred embodiment, the high voltage wide-band amplifier comprises at least one transformer. In another embodiment, the at least one transformer is separate or outside of the high voltage wide-band amplifier, preferably even separate or outside of the card, and the high voltage wide-band amplifier is connected to the primary windings of the at least one transformer. In this embodiment, more than one card can be connected to the at least one, preferably to more than one transformer. In a preferred embodiment, the at least one coreless transformer is a planar transformer, preferably comprising flat windings. Thus, the apparatus of the present invention preferably comprises a planar coreless transformer.

Preferably the high voltage wide-band amplifier comprises more than one coreless electromagnetic transformer, preferably more than two coreless transformers, preferably more than three, five or ten transformers, wherein the at least two transformers are connected in series or in parallel, preferably in parallel. Preferably, the primary windings of the at least two coreless transformers are connected in parallel with one another and the secondary windings of the at least two coreless transformers are connected in series. In a very preferred embodiment, the high voltage wide-band amplifier comprises three or five coreless transformers, wherein the primary windings of the at least two coreless transformers are connected in parallel with one another and wherein the secondary windings of the at least two coreless transformers are connected in series. The high voltage wide-band amplifier further comprises a power driver, preferably a power transistor or a high power semi-conductor, for providing or generating high power current, preferably 1 to 50 amperes (A), more preferably 10 to 40 amperes, at the primary windings of the at least one transformer.

The big advantage when using more than one coreless transformer wherein the primary windings of the at least two coreless transformers are connected in parallel with one another and wherein the secondary windings of the at least two coreless transformers are connected in series is that with such transformers higher voltage can be generated than with only one coreless transformer. For generating the same amount of voltage with only one coreless transformer, many secondary windings would be needed. This would make the transformer bigger than when using more than one transformer. For the apparatus of the present invention, a transformer which is as small and as light weight as possible is desired. Therefore at least two coreless transformers are preferred. Due to such coreless transformers of the invention, it is possible to generate signals of a high voltage over a wide frequency range. With prior art transformers it is not possible to generate many different discrete frequencies over a wide frequency range at high voltage and with high current.

The means for receiving and processing response signals received from the transducer preferably comprises signal conditioning means such as a tension divider and/or a tension limiter. The signal conditioning means are preferably connected to an analog to digital converter module which forwards digital response signals to a computer memory.

The use of a tension limiter and a tension divider, or voltage limiter and voltage divider respectively, enable to determine an accurate echo signal with low signal to noise ratio. The tension limiter limits the tension to a certain predetermined level, for example to ±10 V. This level is chosen as such that the voltage amplitude of the echo signal, respectively the transmission signal, is completely within the voltages range spanned by this limiters. The tension divider reduces the amplitude of the electrical signal by a division of a predetermined factor, for example by a factor 10. The factor is chosen as such that the voltage range of the divided signal is in the range of, preferably identical to, the voltage levels of the limited signal.

The card generates pulses at high tension which means high voltage of e.g. more than 100V, 200V or even more than 1000V and has a maximum repetition rate of about 1 ms. The pulse frequency can be adjusted from between 100 Hz to 1 MHz or from between 1 kHz to 1 MHz, more preferably from between 100 Hz to 10 MHz or from between 1 kHz to 10 MHz, more preferably from between 10 Hz to 10 MHz, more preferably from between 1 Hz to 10 MHz, and most preferably from between 1 Hz to 100 MHz or even from between 1 Hz to 200 MHz. Thus, the card of the invention can be used over a broad range of frequencies including frequencies of infrasonic waves below 20 Hz, which is below that of audible sound waves for humans, frequencies of audible sound waves, i.e. from 20 Hz to 20 kHz and frequencies of ultrasonic waves above 20 kHz, which is above audible sound waves for humans. Thus, the term "wide-band" with respect to the amplifier means throughout the whole text that the amplifier works and can be used over a broad frequency range, that is over the range of 1 kHz to 1 MHz, or even over the range of 100 Hz to 10 MHz, or from 10 Hz to 100 MHz or even from 1 Hz to 200 MHz.

The oscillator is able to create several discrete and different frequencies, preferably more than $2^5$, more preferably more than 100, most preferred more than 1000, particularly more than $2^{10}$, or up to $2^{32}$ discrete frequencies without the need of frequency filters. Cards known in the art work at only up to ten different frequencies and need the use of frequency filters. In addition, the card of the invention is portable.

The apparatus of the present invention can comprise more than one card.

The apparatus of the invention further comprises a measuring device for measuring the dynamic elastic modulus by means of sound waves, in particular the compression modulus K, the shear modulus G, the Young modulus E, and the Poisson ratio v of a material to be analyzed such as mineral binder or polymer. As used herein, the term "sound" is meant to refer to infrasound which is sound with a range of frequencies below 20 Hz, which is below that of human hearing, to audible sound which is sound with a range of frequencies between 20 Hz and 20 kHz which is in the range of that of human hearing, and to ultrasound, which is sound with. a range of frequencies above 20 kHz, which is above that of human hearing. In addition, as used herein, the term "acoustic" relates to a sound as defined above.

The measuring device of the invention comprises at least one transducer and means for acoustically coupling the sample of the material to the at least one transducer. Preferably, the means for acoustically coupling the sample of the material to the at least one transducer comprises at least one wave guide. The at least one transducer is in contact with the wave guide, preferably by means of a contacting material, preferably a viscoelastic material such as for example syrup or the like. In a very preferred embodiment, the wave guide is at least partially covered by a coating, preferably a polymeric coating. This coating is brought in direct contact with the material to be analyzed so that when analyzing the material the coating is between the wave guide and the material to be analyzed.

The coating prevents occasional loss of signal by detachment of the material from the wave guide of the measuring device. The coating is selected so as, on one hand, to enhance contact between the material sample and the wave guide and to ensure that the contact is maintained over the whole duration of the measurement, and on the other hand, to facilitate material sample removal from the wave guide after the measurement is complete. After measurement, the coating does not need to be removed from the wave guide. It can be used several times. The coating is preferably a polymeric coating. In one embodiment the polymeric coating is obtained from an addition reaction of monomers or oligomers. Such preferred polymeric coatings are those on a basis of a polyurethane or epoxide resin. Preferred polyurethane based polymeric coatings are obtained from polyisocyanates, especially from polyisocyanate group containing prepolymers, and water or polyamines or polyols. Preferred polymeric coatings based on epoxide resins are obtained from the reaction of a resin component, which comprises a diglycidylether of bisphenol-A, and/or of bisphenol-F, and/or of bisphenol-A/F, preferred of bisphenol-A, and a hardener component, which comprises a polyamine and/or polymercaptane. These polymeric coatings are preferably used when the material to be analyzed is a mineral binder. In a particularly preferred embodiment, the material to be analyzed is shotcrete and the coating is a polymeric coating based on epoxide resin.

In another embodiment the coating is a polymeric coating which shows releasing properties towards reactive materials. Such coating may comprise or consist of, without limitation, fluorinated hydrocarbons such as polytetrafluorethylene (also known as Teflon®), silicones, or polyolefines such as polypropylene or polyethylene, or nanoparticles or self assembly monolayers molecules, such as silanes, titanates or zirconates, for example those leading to a "lotus flower effect". These polymeric coatings are preferably used when the material to be analyzed is a polymer.

Preferably, the polymeric coating has reactive groups which leads to a chemical bonding or chemical affinity between the coating and the material to be analyzed as well as the wave guide. Therefore, no pressure is needed to ensure the contact between the material to be analyzed and the wave guide. This is an advantage over the state of the art solutions where the material to be analyzed needed to be pressed onto the wave guide to allow measurement, as described e.g. in U.S. Pat. No. 4,754,645.

When the material to be analyzed is already solid and has substantial surface roughness, it is advantageous if the coating further comprises a viscoelastic material which is used between the polymeric coating of the wave guide and the material to be analyzed.

The polymeric coating may also be prepared in situ, i.e. a mixture comprising the monomers or oligomers is located between the wave guide and the material to be analyzed so that the monomeres are reacting during the measurement. The monomers or oligomers are preferably selected as such that the reaction to form the coating is fast. It is preferred that only little energy is dissipated during this reaction in order to alter the kinetics of the curing of the material to be analyzed as little as possible. The in situ formation of polymeric coating is preferably used in case of measuring materials which are already solid and have substantial surface roughness. This helps to guarantee a good contact between the wave guide and the material to be analyzed.

The thickness of the coating is preferably less than 200 μm, more preferably less than 100 μm, less than 50 μm or even less than 10 μm. During measurement, the thickness of the coating must be thinner, preferably about ten times thinner than the sound wave length so as not to introduce additional reflections or signal distortions. For example, for the frequency of 1 MHz and the sound speed of 1482 m/s, the wave length is 1.48 mm and, thus, the thickness of the coating must be thinner than 1.48 mm, preferably thinner than 0.148 mm.

The wave guide, which comprises or preferably consists of poly(methyl(meth)acrylate) or aluminum, comprises one or more than one layer. In case of more than one layer, the different layers are joint by a joining material, preferably an adhesive. If the wave guide comprises more than one layer, the layers are either of the same material or of different material. Thus, in one embodiment, the wave guide comprises a first and a second layer and the first layer is of different material than the second layer. The thickness of the at least one wave guide is preferably chosen to be thick enough to ensure that the emitting pulse (I) and the reflecting pulse (II) in echo mode, respectively the emitting pulse (I) and the transmission pulse (III') in transmission mode, are not overlapping.

The measuring device of the present invention comprises one or more than one transducer. In a preferred embodiment, the measuring device comprises at least a shear or at least a compression transducer. In a particularly preferred embodiment, the measuring device comprises a shear transducer and a compression transducer. When using the shear transducer, the shear modulus can be analyzed, whereas using the compression transducer, the compression modulus can be analyzed. In transmission mode, two transducers of the same type, e.g. two shear transducers or two compression transducers, are arranged opposite each other with the material to be analyzed in between. In case of more than one different transducer, the different transducers may be arranged side by side. Transducers are piezoelectric components, which transform the electric pulse to a mechanical pulse of the same frequency. This pulse propagates through the wave guide to its interface with the material sample. A part of it is reflected toward the emitting transducer while the other part is transmitted through the material. This transmitted pulse may be captured by another transducer usually of the same type as the emitting transducer which transforms the transmitted acoustic wave back into an electrical signal. In a reflection or echo mode, the same transducer acts both as emitter and receiver and therefore transforms the reflected acoustic wave back to an electrical signal. Thus, in a very preferred embodiment, the measuring device comprises at least one transducer of one type, wherein said at least one transducer is used as emitting and receiving transducer.

In another embodiment, the measuring device comprises at least two transducers of the same type, wherein one transducer is used as emitting transducer and the other transducer is used as receiving transducer.

The more different transducers are used, the more different aspects of a material can be analyzed. However, the present invention does not need more than one transducer of one type to work over a broad frequency range. One transducer of one type is enough to work over a broad frequency range.

The sound speed propagation in materials depends on temperature. For example in water the sound speed is 1482 m/s at 20° C. and 1530 m/s at 40° C. Therefore, the temperature has to be controlled and/or measured for increased accurateness. Thus, in a further embodiment, the measuring device comprises a temperature measuring element, preferably a thermocouple, which allows to measure the temperature within the material to be analyzed.

The measuring device of the present invention is either directly brought in contact with the material to be analyzed, i.e. is placed on the surface of a material comprising a mineral binder or a polymer, or the measuring device further comprises a means for receiving and holding the sample of a material, that is a means for taking up the material to be analyzed. The means for receiving and holding the sample of a material may be for example an open cell or a tube. Preferably, the means for receiving and holding the sample of a material is ring-shaped. The means for receiving and holding the sample of a material can also be in shape of a tube. In this embodiment the material in the tube can be analyzed. Such an embodiment is especially useful for analyzing continuously the material in the tube and may be used for an in-process quality or a reaction control of reactive polymers or oligomers which might be raw materials, intermediates or final products. The tube is preferably a transport pipe, a reactor vessel or a by-pass pipe. The tube may be of a material comprising or consisting of metal, preferably stainless steel, or of a polymer material. In one embodiment, the wave guide is introduced into an opening of said tube in such a manner that the void between tube and wave guide is sealed to avoid material from leaving the tube. Preferably, the surface of the wave guide which is inside the tube is flat. Alternatively, the surface of the wave guide which is inside the tube is in the shape of the tube curvature. In another embodiment, the wave guide can be placed at the exterior of the tube. The surface of the wave guide which is in contact with the tube can be in the shape of the tube curvature. Alternatively, the wave guide can comprise a further layer which preferably is of the same material as the tube, and which preferably is in the shape of the tube curvature on the side where the layer of the tube material is in contact with the tube. On the other side, where the further layer of the wave guide is in contact with the other part of the wave guide, the further layer is preferably flat. In yet another embodiment, the section of the tube is flattened where the measurement is performed and where the wave guide is either introduced into the tube or is placed outside of the tube. Preferably, this can be realized in that the whole tube section is flattened or pressed, respectively. In one embodiment, where the wave guide is outside of the tube, the tube preferably contains a section with flat protuberances at the inside and the outside of the tube so that the signal from the wave guide is not deviated by a surface which is not flat.

The means for receiving and holding the sample of a material optionally comprises more than one compartment, preferably two compartments, preferably separated by a separating wall. If two compartments are used, it is preferred that one compartment is in contact with the material to be analyzed whereas the other one is empty enabling measurement of an empty compartment as control in parallel with the measurement of the material and therefore enabling direct comparison. Another advantage of more than one compartment or more than one device is that the means comprising the empty compartment does not need to be emptied between measurement. The measuring device comprising more than one compartment may comprise one transducer for the whole measuring device or more than one transducer, preferably one transducer for every compartment. In another embodiment, more than one measuring device is used for the determination of the dynamic elastic modulus of a material, at least one measuring device comprising an empty means for taking up the material to be analyzed or a means not being in contact with the material to be analyzed, and at least one measuring device comprising a means with the material to be analyzed or a means being in contact with the material to be analyzed. Preferably, the means for taking up the material to be analyzed is made of a thermoconductive material.

In a preferred embodiment, the means for taking up the material comprises at least one temperature control element, preferably at least one Peltier element which acts as a thermostat for the material to be analyzed.

The measuring device of the invention may in particular be designed to allow the material to be analyzed to be placed in various ways such as pouring, stamping or spraying and that the contact at the interface with the wave guide is significantly enhanced with respect to the wave guide thanks to the appropriate coating.

The measuring device can be used for measuring the dynamic elastic modulus, in particular the compression modulus K, the Young modulus E, and the shear modulus G and to calculate other physical parameters which are derivable from the dynamic elastic modulus such as for example the Poisson ratio $v$, the viscosity, the glass transition temperature ($T_g$), and the like, of a material to be analyzed such as mineral binder or polymer. Compression modulus K, Young modulus E and shear modulus G as well as Poisson ratio $v$ are basic material properties that can be calculated with the measurement of the longitudinal ($V_l$) and the transversal ($V_t$) speed of acoustic wave propagation in a medium:

$$E = \rho V_t^2 \frac{3V_l^2 - 4V_t^2}{V_l^2 - V_t^2} \quad G = \rho V_t^2$$

-continued $$K = \rho \frac{3V_l^2 - 4V_t^2}{3} \quad v = \frac{V_l^2 - 2V_t^2}{2(V_l^2 - V_t^2)}$$

where $\rho$ is the density of the medium. There are two different possibilities to determine the sound speed: (1) by measuring the transit time t of a wave through a sample of length d, the speed is then given by V=d/t; or (2) by measuring the acoustic impedance Z of the material, which characterizes the resistance of the materials to sound propagation and is linked to density and speed through: Z=$\rho$V. In case the material to be analyzed is a soft material or a material evolving from a soft or liquid state to a solid state, transmission time measurement is not adequate and measurements in echography are preferred and the treatment by acoustic impedances is used.

Between two materials of different impedances, one portion of the wave is reflected while the other is transmitted. In the echo mode the transducer acts as an emitter and a receptor of waves at the same time. At time t=0, the transducer emits a sonic pulse, preferably an ultrasonic pulse, which propagates into the waveguide and reaches the wave guide/material sample interface or in case that the wave guide is coated, at the material sample/coating interface without prior reflection in the case of a single layer wave guide. A part of the wave is reflected at the material sample/wave guide interface, or, if the wave guide is coated, at the material sample/coating interface and goes back to the transducer (see for example interface II of FIG. 5a). The other part of the wave goes through the material sample and then is reflected at the other side of the material at the material sample/air interface (which in case of FIG. 5a is denoted interface III). Alternatively, the interface at the other side of the material than the wave guide may be the interface between the material sample and a lid of the sample container, or between the material sample and another wave guide, or between the material sample and another transducer. Regardless of the exact nature of that interface, this results into two pulse responses at the time $2t_1$ and $2(t_1+t_2)$ (as an example see FIG. 5b). The pulse magnitude coming from the first interface reflection-second pulse at $2t_1$ – is linked to the acoustic impedances of the two mediums. The amplitude of the incident wave $A_i$ at the interface material sample/wave guide is equal to the sum of the amplitude reflected $A_r$ and transmitted $A_t$ at this interface (no dissipation at the interface). The reflection coefficient r and the power coefficient of reflection R, which are the ratio, respectively the square ratio of the amplitude of the reflected wave $A_r$ to the incident wave $A_i$ are linked to the acoustic impedances of the two mediums:

$$r = \frac{A_r}{A_i} = \frac{Z_2 - Z_1}{Z_2 + Z_1}; r = \sqrt{R}$$

$$R = \left(\frac{A_r}{A_i}\right)^2 = \left(\frac{Z_2 - Z_1}{Z_2 + Z_1}\right)^2$$

$A_r$ and $A_i$ are not known since they are the amplitudes arriving at and reflected from the wave guide/sample interface. The reflected signal is attenuated crossing the wave guide back towards the transducer. However, if the reflected pulse is measured previously (or in parallel) in absence of a sample, then because of the large differences of acoustic impedances between the wave guide and air, the entire acoustic energy is reflected. Thus, the echo signal in absence of a material sample is equivalent to the signal that reaches the wave guide/material sample interface but is attenuated by crossing the wave guide back to the transducer. This means that equivalent to $A_r/A_i$ is given by the ratio of the pulse amplitude in presence and in absence of sample.

The most accurate determination of impedances from the above relations involves determining R from the ratio of the integrals of the square of pulse in presence and in absence of a sample in the measuring cell. This measurement is more precise than the measure of r based on the height of the pulse. The dynamic elastic modulus of the material sample can be established with the knowledge of the acoustic impedance of the wave guide and the measure of R.

In case where transmission is measured, a second transducer which acts as a receptor is located on the side of the material sample which is opposite the first transducer for example at the material sample/air interface (see for example interface III in FIG. 5a). This results into two pulses, the emitting pulse at time t=0 and the transmission pulse originating from the material sample/air interface III' at time $t_1+t_2$. In transmission mode, it is preferred that the corresponding emitting and receiving transducers are identical. The receiving transducer then receives the pulse which reaches the material sample/air interface and converts the acoustic signal back into an electrical signal.

In a further aspect, the present invention provides a measuring device comprising at least one wave guide and at least one transducer, wherein said transducer is in contact with said wave guide, characterized in that said wave guide is at least partially covered by a coating, preferably a polymeric coating, preferably on basis of a polyurethane or epoxide resin. The measuring device of the present invention comprises a wave guide, transducer, and coating as hereinabove described.

In the case of reactive materials such as materials comprising mineral binders or polymeric substrates such as adhesives, sealants or floor, the signal evolves with time and therefore sound propagation measurement, in particular ultrasound propagation measurement provides a continuous, non destructive measurement of the dynamic elastic modulus of a material.

In one embodiment, the apparatus of the invention comprises more than one measuring device, preferably one measuring device not being in contact with the material to be analyzed as a control, and one measuring device comprising or being in contact with the material to be analyzed.

In one embodiment, the apparatus preferably further comprises computer means and a computer-readable medium for controlling said means for receiving and processing response signals received from the transducer and/or for controlling said means for generating signals of high voltage.

In a further embodiment, the apparatus of the present invention comprises a power supply. The power may be electricity, battery, or the like.

In yet a further embodiment, the apparatus further comprises a multiplexer unit comprising m gates for transferring transmitted or received signals, m being the number of gates; with each gate being connected to a transducer $t_y$, wherein y is a varying index. The multiplexer unit is preferably connected with the transducer of the measuring device through a cable connection.

Preferably, the apparatus is portable. As used herein, the term "portable" is meant to refer to the total size of an apparatus which can be carried by one person. Preferably, the apparatus without the measuring device, more preferably the whole apparatus including the measuring device, has a volume of less than 100 $dm^3$, preferably less than 10 $dm^3$, even more preferably less than 1 $dm^3$, and preferably the weight of the apparatus without the measuring device, more preferably the whole apparatus including the measuring device, is below 100 kg, more preferably below 10 kg, even more preferably below 2 kg. In a most preferred embodiment, the apparatus without the measuring device, more preferably the whole apparatus including the measuring device, has a volume of less than 1 $dm^3$ and a weight of below 2 kg. Therefore, it is advantageous, if the analog to digital module is integrated in the card of the invention. In particular, it is preferred if the multiplexer unit comprises the card of the invention, preferably the card comprising the analog to digital module. In an even more preferred embodiment, the computer-readable medium is integrated in the multiplexer unit or the card of the invention. In a further embodiment, the apparatus further comprises a display unit, preferably a touch screen, or optionally a display unit and a data entry unit such as keyboard or keypad. In another embodiment, the card of the invention is connected to a computer, preferably a laptop computer. The connection between the card and the computer may be via cable or wireless. Wireless connection is achieved by using a sender and receiver, e.g. via infrared or radio wave connection.

The apparatus of the invention needs less power than ultrasonic measuring devices known in the art. A sufficient power supply is for example the battery of a laptop computer or a battery inside the multiplexer unit. This makes the apparatus of the invention particularly portable and therefore useful for on site measurement of material applications.

The material to be analyzed by the apparatus of the present invention is a material comprising a mineral binder, ceramic or a polymer. Preferably, the mineral binder is a hydraulic binder such as cement or gypsum. In a preferred embodiment, the material is mortar or concrete, in particular shotcrete. The polymer is preferably a reactive prepolymer or oligomer. As used herein, by reactive prepolymer or oligomer is meant that these prepolymers or oligomers have functional groups which are capable of undergoing chemical reactions, particularly cross-linking. In one embodiment, the polymer is or comprises a isocyanate group containing polyurethane prepolymer. In another embodiment the polymer is or comprises a silicone containing alkoxy silane and/or silanolcarboxylic ester groups. In a further embodiment the polymer is or comprises a prepolymer or oligomer containing glycidylether groups, such as glycidylether of bisphenol-A, and/or of bisphenol-F, and/or of bisphenol-A/F. In a further embodiment the polymer is or comprises a prepolymer or oligomer containing (meth)acrylate groups. In a further embodiment the polymer is or comprises a prepolymer or oligomer containing double bonds, such as for example vulcanizable rubbers. These reactive polymers are especially suited for the use in the production of adhesives, sealants, coatings or floors.

In yet a further aspect of the present invention, a method is provided for determining the dynamic elastic modulus of a sample of a material, in particular of mortar or concrete, particularly shotcrete, or of a polymer or ceramic, by means of sound waves, with an apparatus of the invention. Thus, a method is provided for determining the dynamic elastic modulus of a material to be analyzed, the method comprising using the apparatus of the invention. The method preferably further comprises the step of analyzing the signal transmitted or reflected by the measuring device of the invention.

Preferably, the method for determining the dynamic elastic modulus of a material comprises the steps of: (A) selecting a minimum frequency $f_{min}$ and a maximum frequency $f_{max}$, and a number of frequencies n; (B) sending data to the card of the invention for creating a first signal which is preferably transmitted to a multiplexer unit comprising m gates, m being the number of gates; (C) preferably selecting a gate $g_y$ which is connected to a transducer $t_y$, wherein y is a varying index; (D)

isolating a frequency $f_x$ from the range Of $f_{min}$ to $f_{max}$, wherein x is a varying index; (E) transmitting the first signal into the measuring device of the invention, leading to propagate sound, preferably ultrasound energy into a wave guide; (F) receiving a second signal from the transducer originating from the sound energy, preferably the ultrasound energy, being transmitted or reflected from the wave guide or the material to be analyzed; (G) saving said second signal for the corresponding frequency $f_x$; (H) analyzing said second signal to determine amplitude and phase of the received sound, preferably ultrasound energy; (I) evaluating the real time evolution of the amplitude, phase and energy evolution, and optionally the temperature evolution; (J) increasing the varying index x by 1 and repeat the steps (B) to (I) until x is equal to n, n being the number of frequencies selected in step (A); (K) preferably increasing the varying index y by 1 and repeating the steps (B) to (J) until y is equal to m, m being the number of gates; (M) comparing amplitudes, phases, and energy evolutions of the second signals obtained from the measurement without the material to be analyzed to the amplitudes, phases and energy evolutions of the corresponding second signals obtained from the measurement wherein said measuring device is in contact with the material to be analyzed; (N) calculating the dynamic elastic modulus from the comparison made in step (M).

In one embodiment, steps (B) to (K) are performed with a measuring device not being in contact with a material to be analyzed, and then, in a second measurement, the method further comprise a step (L) between step (K) and step (N), the step (L) repeating steps (B) to (K), wherein the measuring device is in contact with a material to be analyzed.

In another embodiment, steps (B) to (K) are performed in parallel for a measuring device with and without material to be analyzed.

Preferably, the steps are controlled by means of a computer program.

The apparatus, device and method of the invention can be used for determining the dynamic elastic modulus for a material comprising mineral binders as well as for polymers, in particular reactive polymers or oligomers as well as for their cured products. In particular, the method is especially suitable to monitor the curing in real time. The apparatus, device and method of the invention can also be used as a tool to control the quality of raw material, intermediate and final product. It may be used as quality control or process control tool. If used for this purpose it is preferred that the measuring device is attached to a tubing or comprises a tube shaped means for taking up the material, in which the reactive polymer or oligomer is transferred.

In a further aspect, the invention provides the use of the apparatus of the invention for the analysis of the dynamic elastic modulus of a material to be analyzed, preferably of a material comprising a mineral binder or of a polymer. Preferably, the mineral binder is a hydraulic binder such as cement or gypsum, and the material is mortar or concrete, particularly preferred is shotcrete. The polymer is preferably a polymeric substrate such as adhesive, sealant or floor.

In yet another aspect, the invention provides the use of an opto-electronical multiplexer unit in an apparatus of the invention, i.e. a multiplexer unit comprising at elast one opto-electronical switch.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2c shows a schematic horizontal cross section A-A of FIG. 2b through the means for taking up the material to be analyzed;

FIG. 3a shows a schematic representation of one embodiment of an apparatus;

FIG. 4 shows a flowchart of the computer program;

FIG. 6 shows time evolution of the shear modulus of a mortar;

FIG. 7 shows a schematic representation of a high voltage wide-band amplifier comprising three transformers;

Only these elements that are essential for an understanding of the invention are shown.

DESCRIPTION OF THE PREFERRED EMBODIMENTS

Figure 1A:
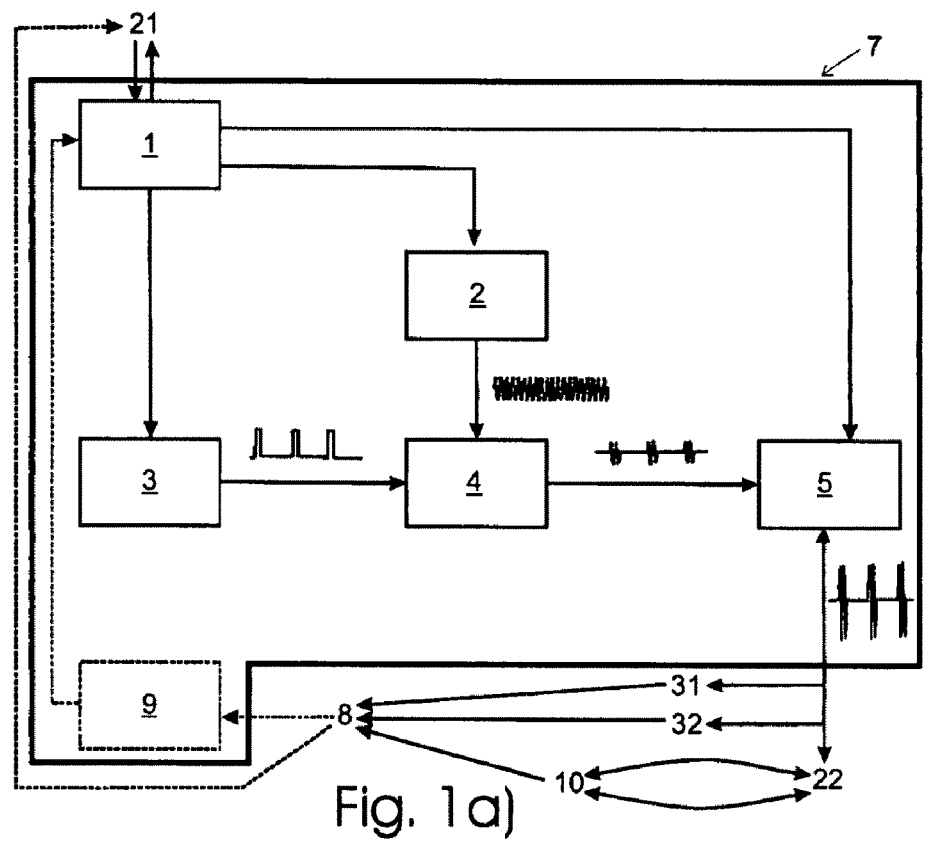
FIG. 1a shows a schematic representation of a card.

Referring now to the drawings, FIG. 1a shows a card 7 in connection with a multiplexer unit 22, a measuring device 10, and an analog to digital module 8, the card comprising a computer bridge interface 1 which sends a signal to a computer-readable medium 21, a low-voltage frequency-adjustable electronic oscillator 2, a signal generator 3, an electronic switch 4, a high voltage wide-band amplifier 5, and optionally an electronic memory 9. In addition, FIG. 1a shows the multiplexer unit 22, the measuring device 10, a tension limiter 31, a tension divider 32, the analog to digital module 8, and a computer-readable medium 21 which are separate from the card 7. The analog to digital module 8 is either a separate unit or part of a computer. The electronic memory 9 (shown in dashed lines) can either be on the card 7 or in the computer. In case that the analog to digital module 8 is part of a computer, preferably also the electronic memory 9 is part of a computer.

An acoustic signal is generated as follows:

The low-voltage, frequency-adjustable electronic oscillator 2 generates a continuous sinusoidal electronic signal at the desired frequency. By low-voltage is meant about 1 to 10 volt (V), preferably 1 V. By frequency-adjustable is meant a frequency in the range of about 1 Hz to about 200 MHz. Working in parallel with the electronic oscillator 2, a signal generator 3 generates a TTL-like (Transistor-Transistor Logic) pulse signal with the desired pulse duration and the desired duty-cycle. The TTL-like pulse has an amplitude of about 1 to 10 V, preferably about 5 V. This signal is sent to an electronic switch 4 and enables or disables the signal generated from the electronic oscillator 2 to be transmitted to a high-voltage wide-band amplifier 5 comprising at least one coreless transformer 33 (not shown in FIG. 1a, but shown in FIG. 7). By high-voltage is meant from about 100 V to about 1 kV or even to about 10 kV. The output of the amplifier 5 is sent through a multiplexer unit 22 to a transducer 12 (not shown in FIG. 1a, but shown in FIGS. 2 and 3) of the measuring device 10 in order to transform the electrical signal into an acoustic signal.

Then the measuring device 10 measures the acoustic signal, preferably the ultrasonic signal, transmitted through or reflected by the material 25 to be analyzed (not shown in FIG. 1a, but shown in FIGS. 2 and 3), as follows:

The transducer 12 is used to convert the acoustic signal, preferably the ultrasonic signal, into an electrical signal. Then this analog electrical signal is sent via the multiplexer unit 22 to the tension limiter 31, which limits tension to for example about 10V, and to the tension divider 32 which divides tension by e.g. a factor 10, and then the signal is converted to a digital signal by the means of an analog to digital signal converter 6 (not shown) in the analog to digital module 8. This digital signal is stored in an electronic memory 9 which is either on the card or in the computer, in order to be transferred to the computer-readable medium 21 directly or via the computer bridge interface 1. The two possibilities are indicated by dashed lines.

The measuring device 10 has also the functionality to measure and to control temperature: one or more temperature measuring element 17 (not shown in FIG. 1, but shown in FIGS. 2 and 3) and/or one or more temperature control element 19 (not shown in FIG. 1, but shown in FIGS. 2 and 3) is connected to the measuring device 10. An analog to digital signal converter 6 (not shown) in the analog to digital module 8 converts the analog signal of the temperature measuring element 17 (not shown in FIG. 1, but shown in FIGS. 2 and 3) and/or the temperature control element 19 (not shown in FIG. 1, but shown in FIGS. 2 and 3) into a digital signal, which is stored in an electronic memory 9.

Figure 1B:
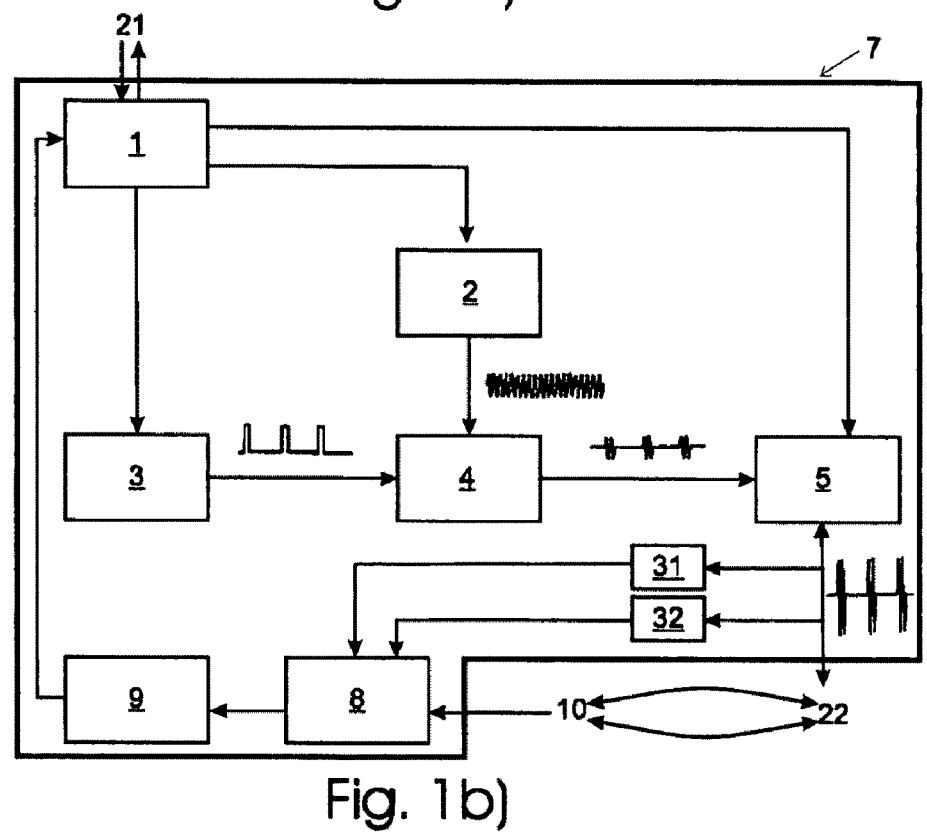
FIG. 1b shows a schematic representation of a card comprising an analog to digital module, a tension limiter, and a tension divider.

According to FIG. 1b, the card 7, as described for FIG. 1a, is shown. In contrast to the card 7 described for FIG. 1a, the analog to digital module 8, the tension limiter 31, and the tension divider 32 are integrated in the card 7.

Figure 1C:
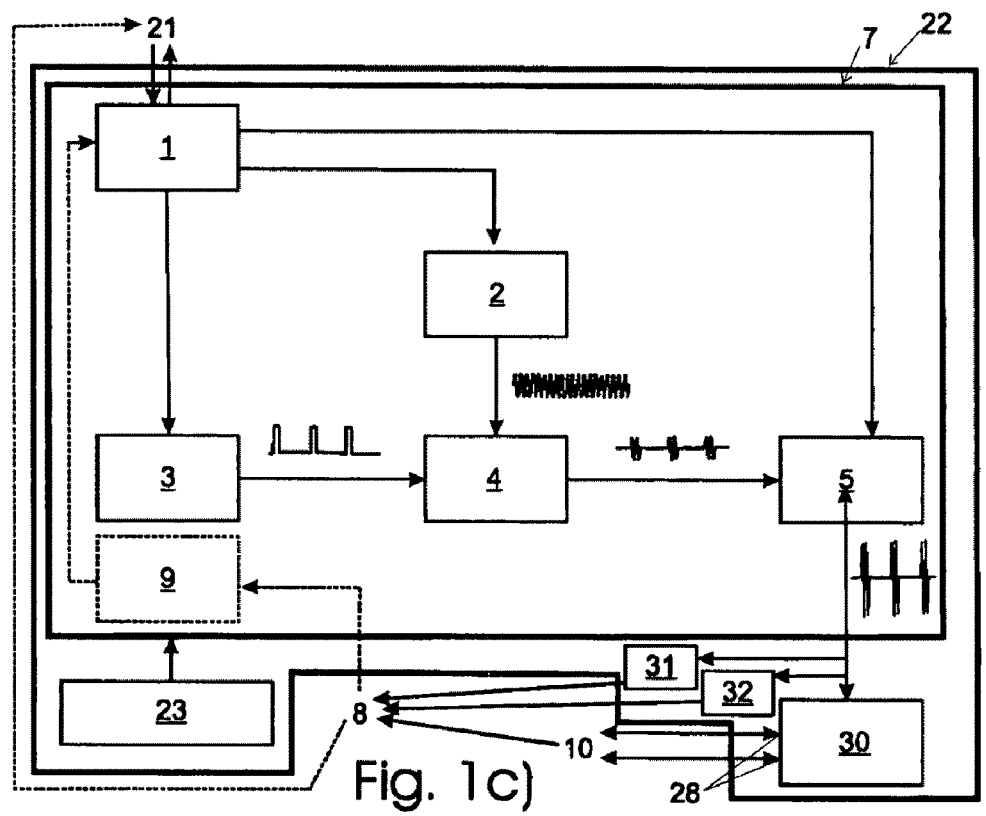
FIG. 1c shows a schematic representation of a multiplexer unit comprising a card, the card comprising a tension limiter, and a tension divider.

According to FIG. 1c, the multiplexer unit 22 comprises the card 7 as described for FIG. 1a, the tension limiter 31, and the tension divider 32. The analog to digital module 8, and the measuring device 10 are separate units. The electrical signal is sent from the high-voltage wide-band amplifier 5 through at least one gate 28 of a switching unit 30 of the multiplexer unit 22 to a transducer 12 (not shown in FIG. 1c) of the measuring device 10 in order to transform the electrical signal into an acoustic signal. Then the measuring device 10 measures the acoustic signal transmitted through or reflected by the material 25 (not shown in FIG. 1c) to be analyzed. The transducer 12 (not shown in FIG. 1c) is used to convert the acoustic signal into an electrical signal, then this analog signal is sent via at least one gate 28 of a switching unit 30 of the multiplexer unit 22 to the tension limiter 31 and the tension divider 32 and then converted to a digital signal by the means of an analog to digital signal converter 6 (not shown) in the analog to digital module 8. This digital signal is stored in an electronic memory 9 which is either on the card or in the computer, in order to be transferred to the computer-readable medium 21 directly or via the computer bridge interface 1. The two possibilities are indicated by dashed lines. The multiplexer unit 22 may optionally comprise a power supply 23.

Figure 1D:
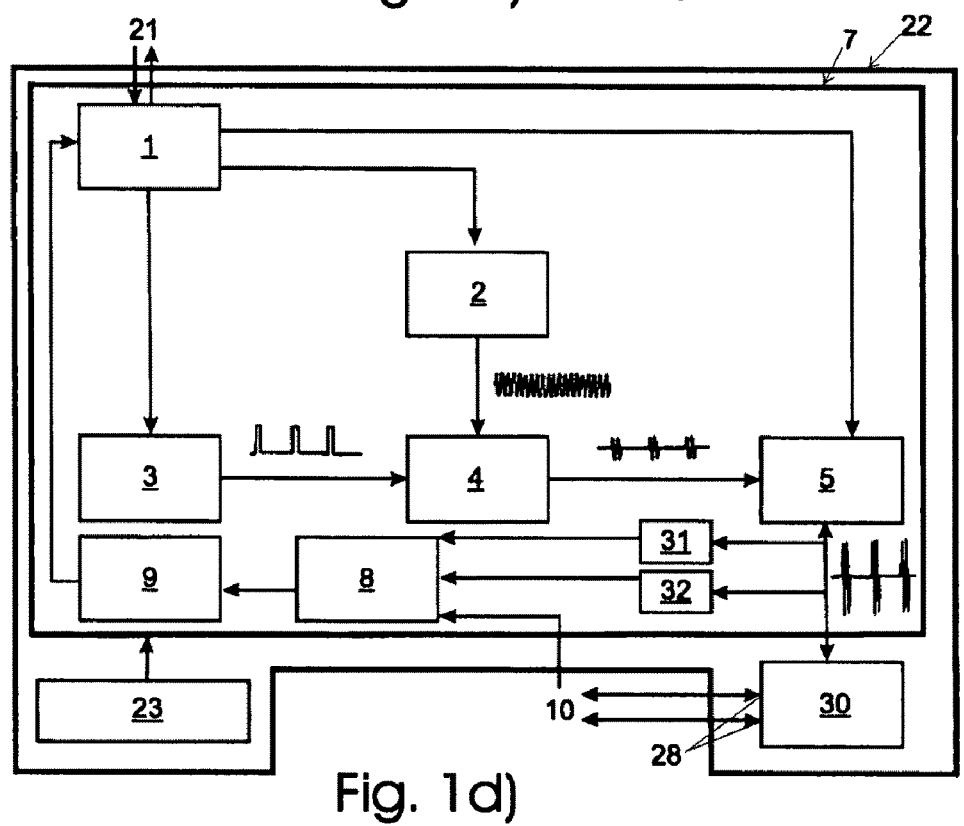
FIG. 1d shows a schematic representation of a multiplexer unit comprising a card, the card comprising a tension limiter, a tension divider and an analog to digital module.

FIG. 1d shows a multiplexer unit 22 as described for FIG. 1c. In contrast to FIG. 1c the analog to digital module 8 is integrated in the card 7 and is not a separate unit.

Figure 1E:
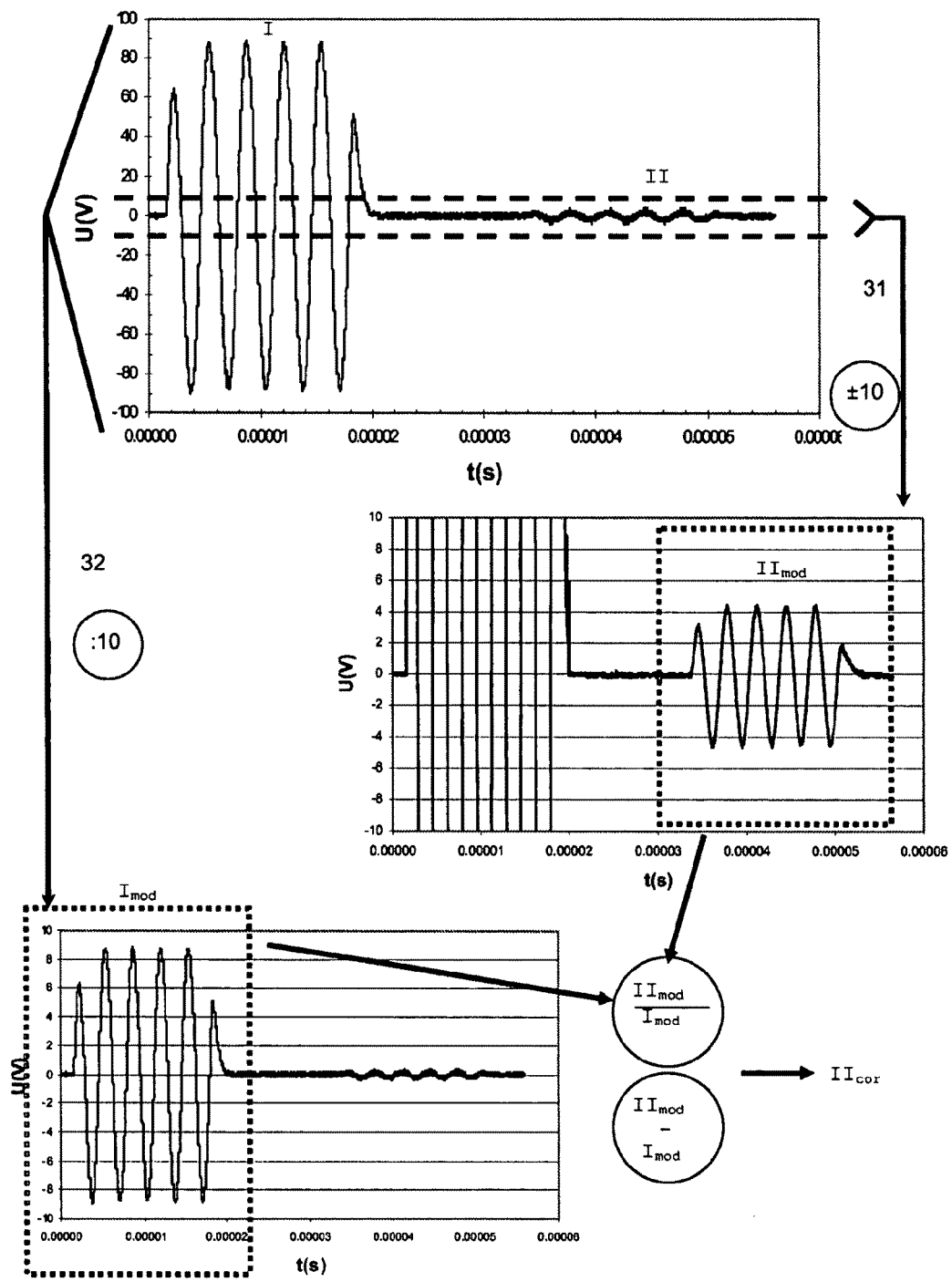
FIG. 1e shows a schematic representation of the working principle of the tension limiter and tension divider

FIG. 1e describes the working principle of the tension limiter 31 and tension divider 32. The electrical signal is taken from the connection between the multiplexer unit 22 and the high voltage wide-band amplifier 5. Due to the high differences in voltage of the excitation pulse I and of the echo pulse II, respectively of the transmission signal III', the direct comparison of the two parts of the electrical signal gives rise to the problem of a low signal to noise ratio.

The use of the tension limiter 31 and tension divider 32 enables to determine an accurate echo or transmission signal with high signal to noise ratio. The tension limiter 31 limits the tension to a certain predetermined level, for example to ±10 V. This level is chosen as such that the voltage amplitude of the echo signal, respectively the transmission signal, is completely within the voltages range spanned by this limiter. The so limited signal is transferred to the analog to digital module 8. This analog to digital module 8 converts the incoming signal to a digital signal using a resolution being determined by a predetermined numbers of discrete level points within the range of the chosen voltage ranges.

The tension divider 32 reduces the amplitude of the electrical signal by a division of predetermined factor, for example by a factor 10. This divided signal is transferred to the analog to digital module 8. The factor is chosen as such that the voltage ranges of the divided signal is in the range of, preferably identical to, the voltage levels of the limited signal.

Within the memory, respectively in the computer, the echo signal, respectively the transmitted signal, is isolated from the limited signal $I_{mod}$ and the excitation pulse is isolated from the divided signal $II_{mod}$. By division of the two isolated signals $II_{mod}$ and $I_{mod}$, a correction of the echo signal $II_{cor}$, respectively the transmission signal $II_{cor}$, is achieved eliminating all signal fluctuation originating from amplitude of the excitation pulse. Phase fluctuation may be reduced by substrating $I_{mod}$ from $II_{mod}$. This leads to an enhancement of accuracy and an enhancement of signal to noise ratio of the echo signal respectively the transmission signal.

Figure 2A:
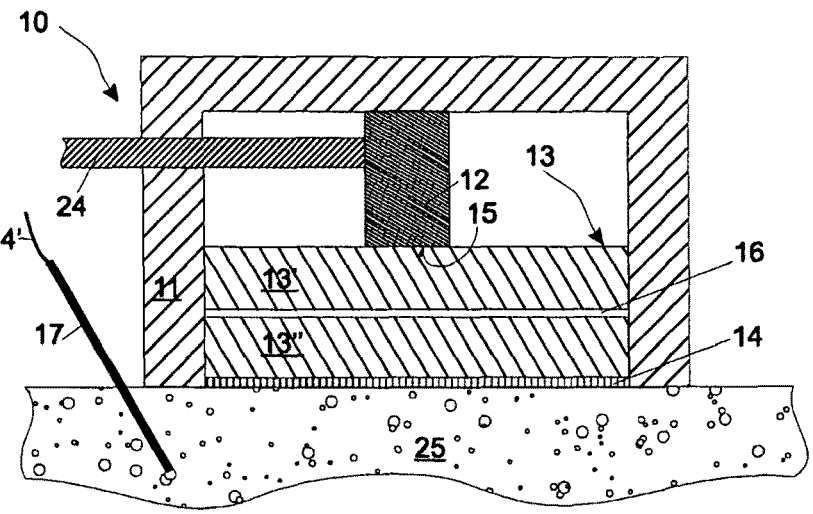
FIG. 2a shows a schematic vertical cross section of a measuring device being brought in contact with a material to be analyzed.

According to FIG. 2a, the measuring device 10 is brought in contact with, or placed on material surface of, a material 25 to be analyzed. Such a measuring device comprises a casing 11, a wave guide 13 with at least one layer, preferably a first layer 13' and a second layer 13", a transducer 12, wherein the transducer 12 is in contact with the wave guide 13 by means of a contacting material 15, preferably a viscoelastic material, and wherein the wave guide 13 at the wave guide 13"/material sample 25 interface is at least partially covered by a coating 14, preferably a polymeric coating on basis of a polyurethane or epoxide resin. FIG. 2a shows a measuring device comprising two layers of a wave guide, a first layer 13' and a second layer 13". The two layers are joint by a joining material 16, preferably an adhesive. The first layer 13' and the second layer 13" are of the same or of different material. FIG. 2a represents only an exemplary embodiment of a measuring device. It is obvious for a skilled person in the art, that the measuring device 10 may comprise only one layer or more than two layers of a wave guide 13 or that the measuring device 10 may comprise more than one transducer 12. The transducer 12 is connected with a multiplexer unit 22 (not shown) by a cable connection 24. The temperature of the material to be analyzed is measured with a temperature measuring element 17, preferably a thermocouple, which is connected with an analog to digital module 8 (not shown) by a cable connection 24'.

Figure 2B:
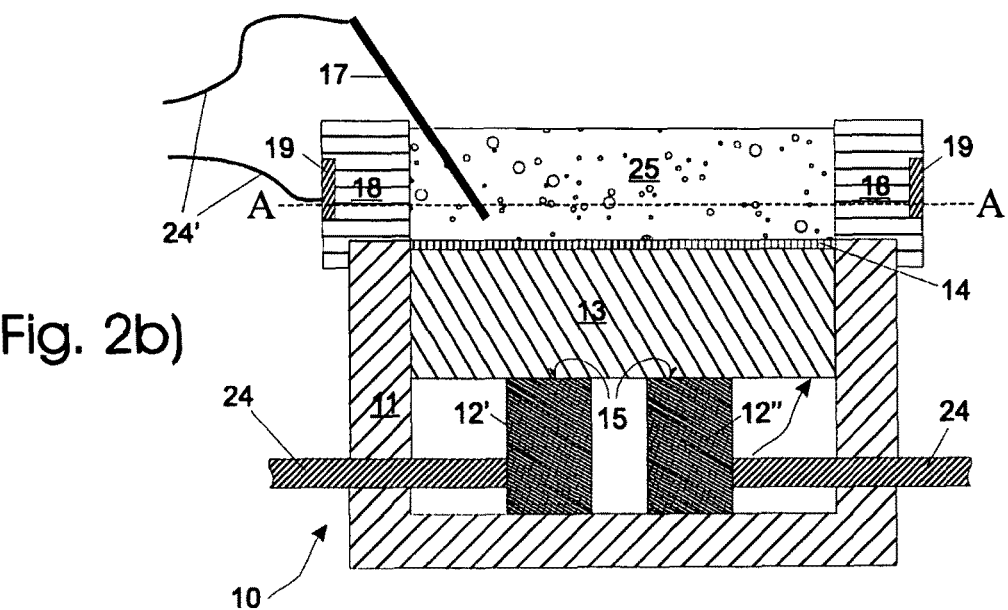
FIG. 2b shows a schematic vertical cross section of a measuring device comprising a means for taking up the material to be analyzed.

FIG. 2b shows a cross section through a measuring device comprising, in addition to the measuring device of FIG. 2a, a means 18 for taking up the material 25 to be analyzed. The means 18 comprises at least one temperature control element 19, preferably a Peltier element, which is used as a thermostat to temper the material 25 to be analyzed. In addition, only one layer of a wave guide 13 and two transducers, a shear transducer 12' and a compression transducer 12" are shown. The temperature measuring element 17 and the temperature control element 19 are connected with an analog to digital module 8 (not shown) by cable connection 24'.

FIG. 2c shows a horizontal cross section A-A through the ring-shaped means 18 for taking up the material 25 to be analyzed. The more than one temperature control elements 19 are preferably connected by cable connection 24". In another embodiment, each temperature control element 19 is connected separately with the analog to digital module 8 by cable connection 24'.

FIG. 3a shows a schematic representation of an apparatus 20 for determining the dynamic elastic modulus of a material by means of sound waves comprising a computer-readable medium 21 which is preferably part of a computer or laptop computer, the card 7 as described in detail in FIG. 1b comprising an analog to digital module 8 (not shown), a multiplexer unit 22, and the measuring device 10 of the invention as described in more details in FIG. 2b, which is connected to the multiplexer unit 22 and to the analog to digital module 8 (not shown) of the card 7 by cable connections 24 and 24'. Either the computer-readable medium 21, typically the computer or laptop computer, or the multiplexer unit 22 or both comprise a power supply 23 (not shown). The power may be electricity, battery, or the like. The card 7 is connected to the computer-readable medium, preferably the computer or laptop computer for example via cable or wireless.

Figures 3B, 3C:
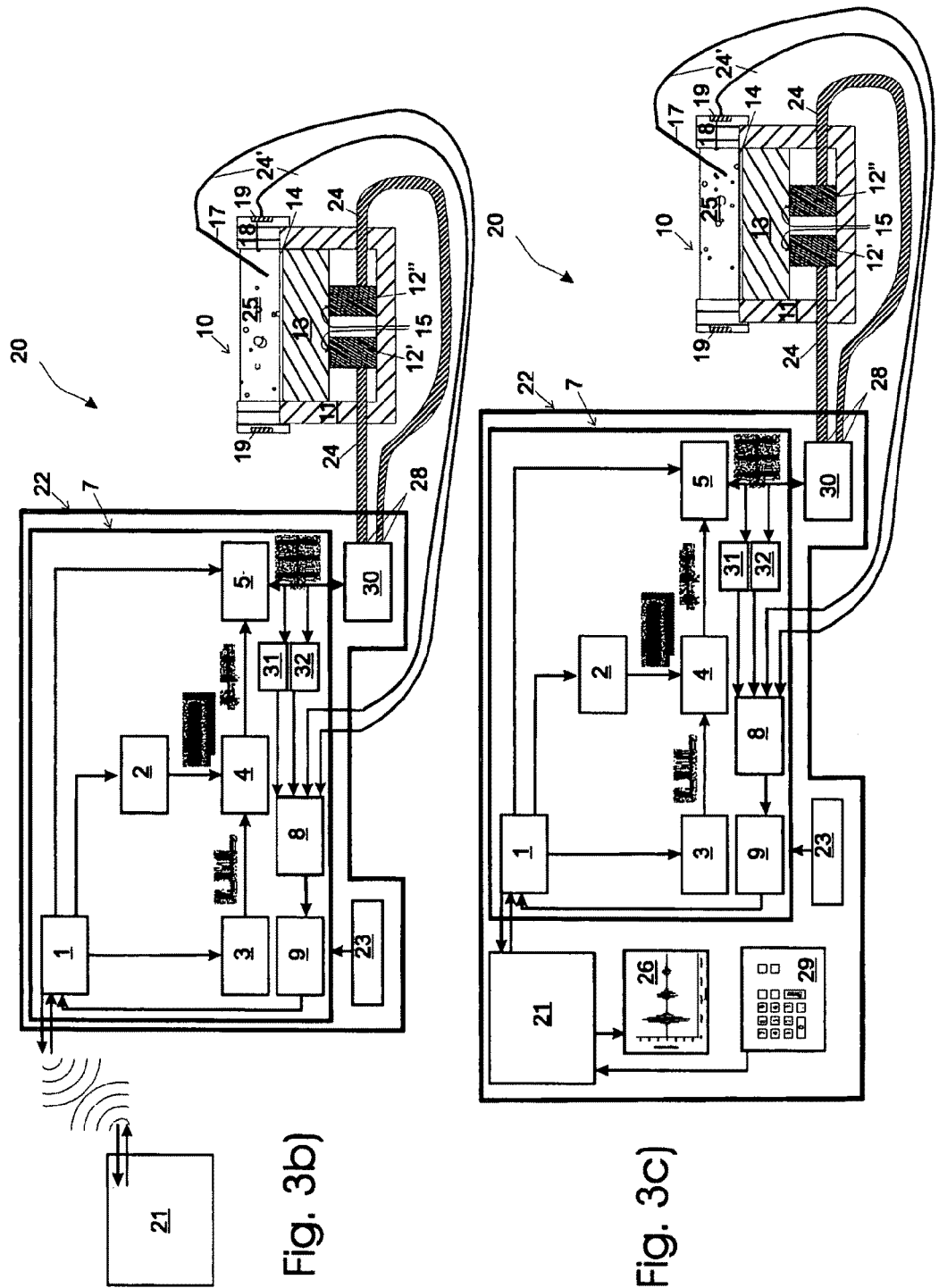
FIG. 3b shows a schematic representation of a second embodiment of an apparatus.
FIG. 3c shows a schematic representation of a third embodiment of an apparatus.

FIG. 3b shows a schematic representation of an apparatus 20 for determining the dynamic elastic modulus of a material 25 by means of sound waves comprising a computer-readable medium 21, the multiplexer unit 22 comprising the card 7 as described in more details in FIG. 1c, and the measuring device 10 of the invention as described in more details in FIG. 2b. The computer-readable medium 21 which is preferably part of a computer or laptop computer is connected to the a multiplexer unit 22 by wireless connection. The multiplexer unit 22 comprises the card 7 of the invention comprising an analog to digital module 8 and a power supply 23. The power supply 23 may also be part of the computer or laptop computer in addition or instead of the power supply 23 of the multiplexer unit 22. The transducer 12, or as shown here in case of two transducers transducer 12' and transducer 12", of the measuring device 10 is or are connected through gates 28 with a multiplexer unit 22 by a cable connection 24. The temperature of the material to be analyzed is measured with a temperature measuring element 17, preferably a thermocouple, which is connected with an analog to digital module 8 by a cable connection 24'.

FIG. 3c shows a schematic representation of an apparatus 20 for determining the dynamic elastic modulus of a material 25 by means of sound waves comprising multiplexer unit 22 and the measuring device 10 of the invention. The multiplexer unit 22 comprises a computer-readable medium 21, a display unit 26, a data entry unit 29 such as a keyboard or a keypad for entering the instructions, the card 7 as described in detail for FIG. 1c comprising an analog to digital module 8, and a power supply 23. The transducer 12 of the measuring device 10 is connected through gates 28 with a multiplexer unit 22 by a cable connection 24. The temperature of the material to be analyzed is measured with a temperature measuring element 17, preferably a thermocouple, which is connected with an analog to digital module 8 by a cable connection 24'.

FIG. 4 shows a flowchart of the method of the invention which is preferably controlled by means of a computer program. The computer program preferably causes a computer to perform the steps of the method. The method for determining the dynamic elastic modulus of a sample of a material by means of sound waves comprises the steps of (A) selecting a minimum frequency $f_{min}$ and a maximum frequency $f_{max}$, and a number of frequencies n; (B) sending data to the card 7 of the invention for creating a first signal which is preferably transmitted to a multiplexer unit 22 comprising m gates, m being the number of gates; (C) preferably selecting a gate $g_y$, which is connected to a transducer $t_y$, wherein y is a varying index; (D) isolating a frequency $f_x$ from the range of $f_{min}$ to $f_{max}$, wherein x is a varying index; (E) transmitting the first signal into the measuring device of the invention, leading to propagate sound, preferably ultrasound energy into a wave guide; (F) receiving a second signal from the transducer originating from the sound, preferably the ultrasound energy, being transmitted or reflected from the wave guide or the material to be analyzed; (G) saving said second signal for the corresponding frequency $f_x$; (H) analyzing said second signal to determine amplitude, phase, and energy of the received sound, preferably ultrasound energy; (I) evaluating the real time evolution of the amplitude and the phase evolution, the wave energy evolution and optionally the temperature evolution; (J) increasing the varying index x by 1 and repeat the steps (B) to (I) until x is equal to n, n being the number of frequencies selected in step (A); (K) preferably increasing the varying index y by 1 and repeat the steps (B) to (J) until y is equal to m, m being the number of gates; optionally comprising step (L) (shown as dashed line) repeating steps (B) to (K), wherein the measuring device of the invention is in contact with a material to be analyzed; (M) comparing amplitudes, phases and energy evolutions of the second signals obtained from the measurement without the material to be analyzed to the amplitudes, phases and energy evolutions of the corresponding second signals obtained from the measurement wherein said measuring device is in contact with the material to be analyzed; (N) calculating the dynamic elastic modulus from the comparison made in step (M).

Figure 5A:
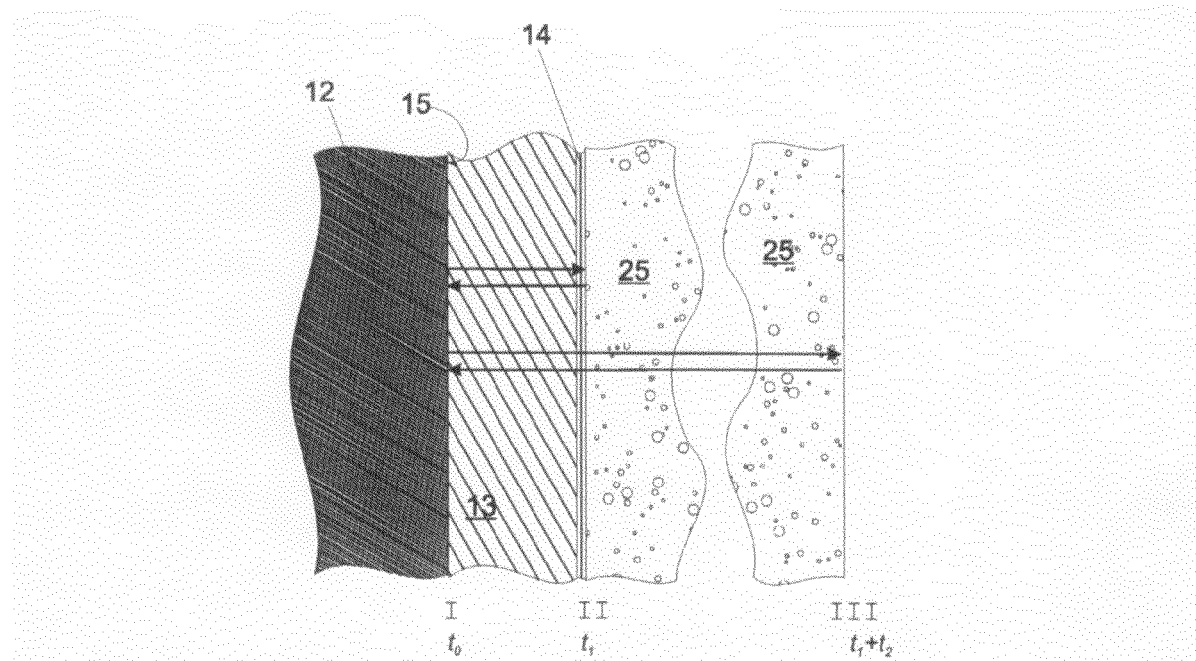
FIG. 5a shows a schematic representation of reflection mode measurement of the sound propagation.

FIG. 5a shows reflection mode measurement of the sound propagation. In the reflection or echo mode the transducer 12 acts as an emitter and a receptor of waves at the same time. At time t=0 at the transducer 12/wave guide 13 interface I comprising a contacting material 15, the transducer 12 emits a sound pulse, preferably an ultrasound pulse, which propagates into the wave guide 13 which comprises one single layer and a coating 14. The sound pulse then reaches coating 14/material sample 25 interface (II) without prior reflection. A part of the wave is reflected at the coating 14/material sample 25 interface II at time $t_1$ and goes back to the transducer 12. The other part of the wave goes through the material sample 25 and then is reflected at the material sample 25/air interface III. This results into the observation of two pulse responses at $2t_1$ and $2(t_1+t_2)$.

Figure 5B:
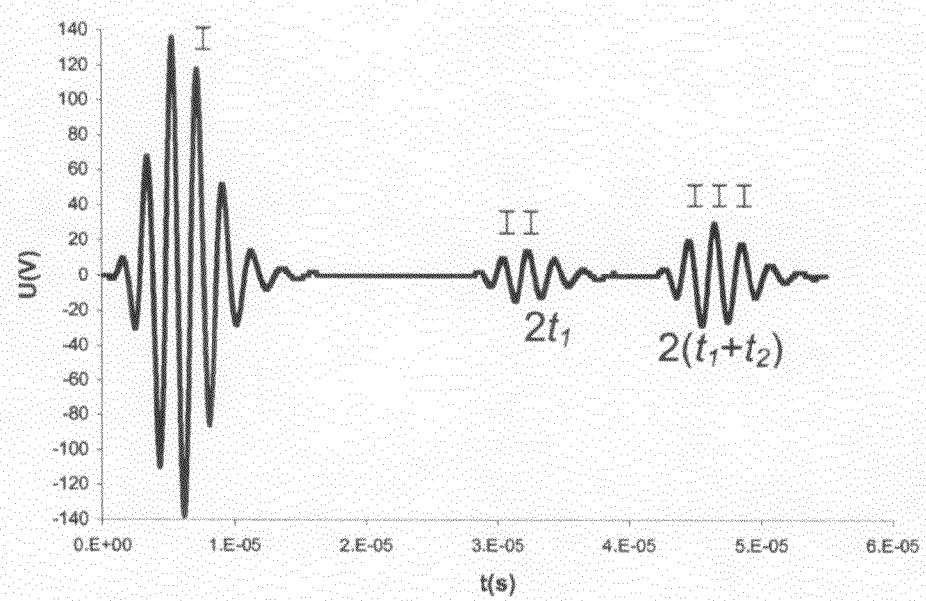
FIG. 5b shows a schematic graph of waves resulting from reflection mode measurement of the sound propagation.

FIG. 5b shows the result of the reflection mode measurement of the sound propagation. The amplitude in voltage (V) vs. time in seconds (s) of three pulses is shown. The first pulse I at $t_0$ originates from the emitting transducer 12, the second pulse II at $2t_1$ originates from the reflection on the coating 14/material sample 25 interface, and the third pulse III at $2(t_1+t_2)$ originates from the material sample 25/air interface.

FIG. 6 shows the development of shear modulus G (Pa) as a function of time t (min) determined by experiments on three mortars. Ex 2 is a mortar of water and a composition consisting of 23.1% by weight of cement, 7% by weight of calcium carbonate, 27.94% by weight of sand (0-1 mm) and 41.96% by weight of sand (1-4 mm).

Ex 3 is the same mortar as Ex 2 apart from it comprising an additional 1% by weight, based on the cement, of the superplasticizer and retarder Sika®ViscoCrete® SC-305 (commercially available at Sika Schweiz). Ex 1 is the same mortar as Ex 3 apart from it comprising additionally 6% by weight, based on the cement, of the accelerator Sigunit®-L53 AF (commercially available at Sika Schweiz). Therefore Ex 1 represents an accelerated mortar, Ex 2 a standard mortar and Ex 3 a retarded mortar.

All mortars have a water/cement ratio of 0.48 and have been applied as wet mixes on the measuring device. Ex 1 has been sprayed at room temperature as a wet shotcrete into a measuring device by a laboratory shotcrete equipment. The measuring device used comprises two transducers, one for measuring the compression modulus and the other for measuring the shear modulus, arranged for echo mode measurement. The wave guides are coated with a layer of 100 micrometer of the epoxide resin which is obtained by curing of a two component resin, the first component comprising a diglycidylether of bisphenol-A and the second component comprising a polyamine. The measuring device is of cylindrical shape with a height of 9 cm and a diameter of 13 cm and a weight of 4 kg. The measuring device is connected to a multiplexer unit as described in more details in FIG. 1c having the dimensions of 10×5×4 cm and has the weight of 300g. The multiplexer is connected by a USB-connection to a laptop computer on which the controlling and calculation program is running in a LabVIEW™ (LabView 7 express, commercially available from National Instruments) environment. The measurements have been made in real time over 100 discrete frequencies in the frequency range of 50 kHz to 5 MHz. From the set of time evolution curves of the shear modulus for the individual frequencies, FIG. 6 shows exemplarily the curve for the frequency of 500 kHz. From this representation one can clearly see that the modulus is increasing as curing proceeds. Furthermore it can be seen from Ex 1 in FIG. 6 that a fast stiffening already in the first minutes as well as an early and faster strength development can be measured.

FIG. 7 shows a schematic representation of a high voltage wide-band amplifier 5 comprising a power driver 36 and three transformers 33A, 33B, 33C. The power driver 36 preferably is a power transistor or a high power semi-conductor for providing or generating high power current, preferably 1 to 50 amperes (A), more preferably 10 to 40 amperes at the primary windings 34 of the at least one transformer. The primary windings 34 of the three coreless transformers are connected in parallel with one another and the secondary windings 35 of the three coreless transformers are connected in series. The low-voltage electronic signal at the desired frequency is transmitted from the electronic switch 4 (shown in FIG. 1a) to the power driver 36 of the high voltage wide-band amplifier 5 and then to the primary windings 34 of the three transformers 33A, 33B, and 33C. The electronic signal is then transmitted to the secondary windings 35 of the three transformers 33A, 33B, and 33C, which are connected in series. Since the secondary windings 35 of each transformer comprise more windings then the primary windings 34 of each transformer, the total voltage of the signal is amplified. The total final output voltage of the signal, that is the sum of the voltages at the secondary windings, is in this case, when three transformers are used, three times higher than when only one transformer would be used. This is due to the fact that the primary windings 34 of the three transformers are connected in parallel and the secondary windings 35 of the three transformers are connected in series. The electronic signal at high voltage, preferably between 100 and 1000V, is then transmitted from the secondary windings 34 of the transformers to a transducer 12 of the measuring device 10 (not shown here).

FIG. 8 shows the development of material properties as a function of time obtained by experiments on a cement.

Figure 8A:
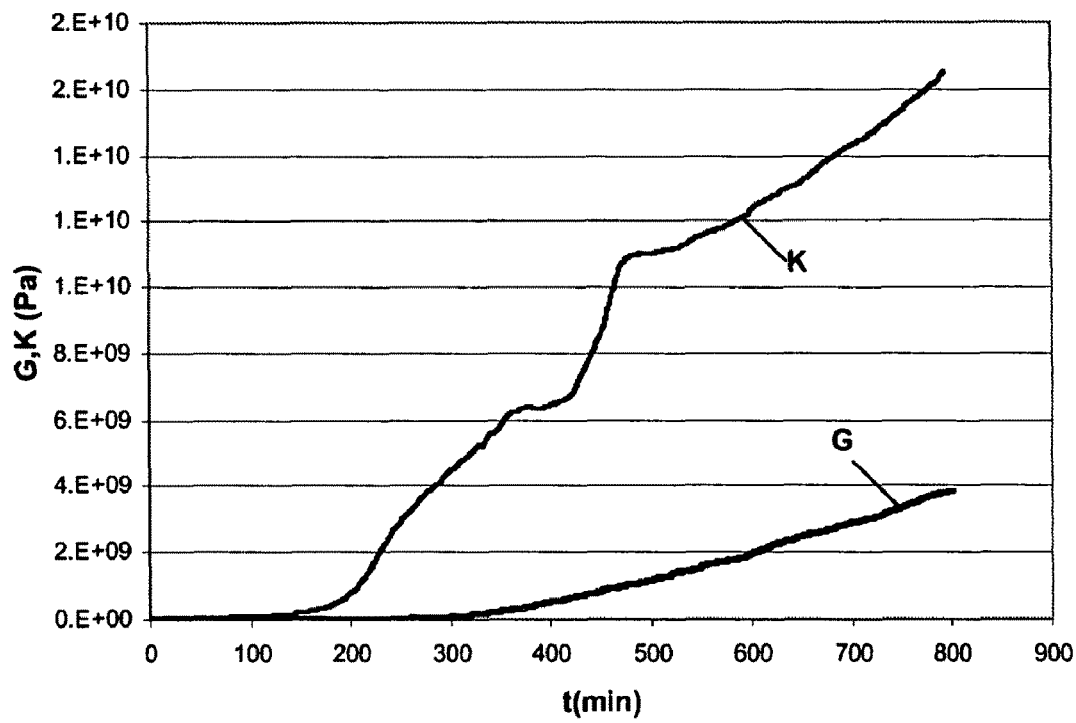
FIG. 8a shows time evolution of the shear and compression modulus of a cement paste.

FIG. 8a shows the development of shear modulus G and compression modulus K of a Portland cement mixed with water in a water/cement ratio of 0.3. The cement/water mix is placed on a measuring device. This device has a ring shaped container and is thermostatized by Peltier elements, which are attached to the ring shaped container, to 25° C. Further details to the measuring device and apparatus used and the measuring are given in the description of FIG. 6. For the experiment 100 discrete frequencies have been used out of a range from 50 kHz to 5 MHz. FIG. 8a displays the curves for 500 kHz.

Figure 8B:
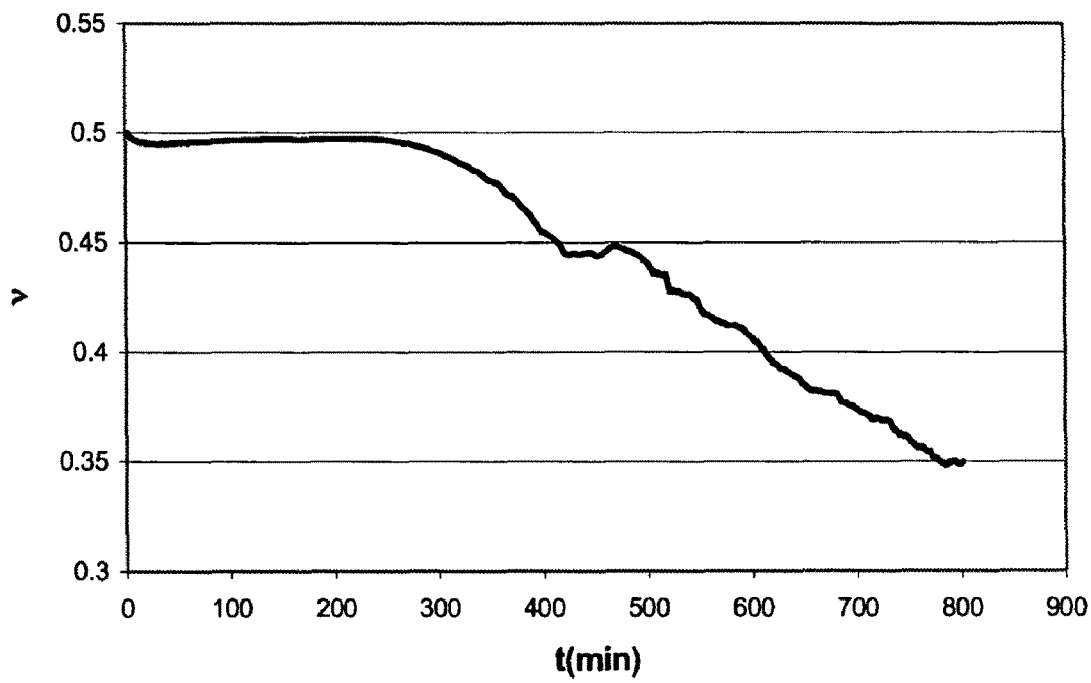
FIG. 8b shows time evolution of the Poisson ratio of a cement paste.

FIG. 8b shows the time evolution of the Poisson ratio ν at 500 kHz, which has been determined from the experimental values measured and discussed in FIG. 8a. FIGS. 8a and 8b clearly show a change of material properties as the cement cures.

Figure 8C:
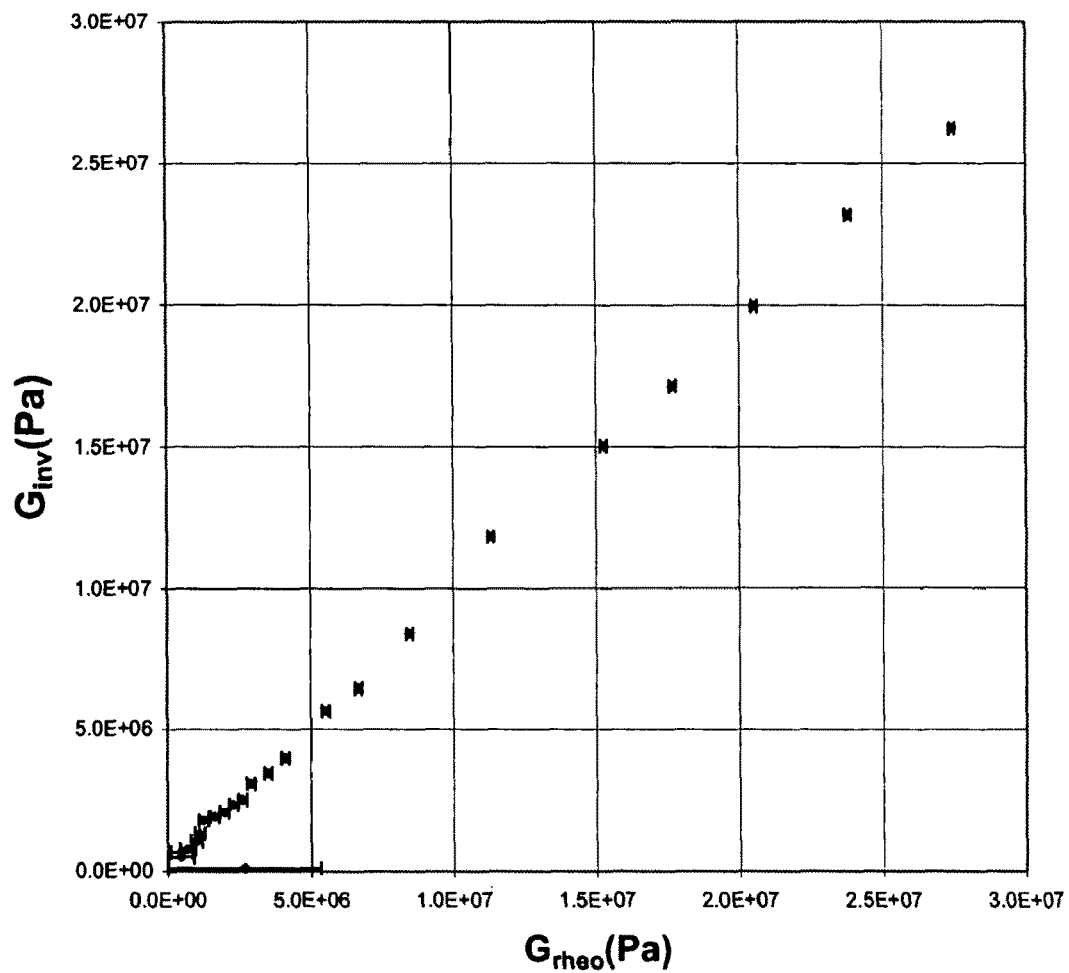
FIG. 8c shows shear modulus values of a cement paste determined by sound measurement and by rheology measurement.

FIG. 8c shows that the comparison of shear modulus G values determined by sound measurement $G_{inv}$ of the example described in FIGS. 8a and 8b with those determined by rheology measurements $G_{rheo}$. For the determination by rheology the sample has been measured on a rheometer Paar Physica MCR300 using rough plate/plate geometry (diameter 50 mm, gap 2 mm), frequency 1 Hz, oscillatory mode, maximum deformation of 0.02% to be in the linear regime at the temperature of 25° C. The individual values of shear modulus values for the selected time points obtained by rheology $G_{rheo}$ respectively $G_{inv}$ by the method of invention are compared by the representation in FIG. 8c. For a good correlation the same value is obtained by the different methods, which is reflected that a point in the representation of the graphic used a point is in the diagonal. The rheology method shows at low curing times a relatively high error in the measurements which is indicated by the error bars in FIG. 8c.

However, the values determined by sound measurement are obtained in real time from one sample whereas the data determined by rheology originate from different samples and are determined not in real-time. Furthermore, it is not possible to measure the compression modulus by a rheometer. The correlation of results obtained by the two different methods is excellent as can be observed from the FIG. 8c.

The invention is of course not restricted to the exemplary embodiment shown and described.

Obviously, numerous modifications, combinations, and variations of the present invention are possible in light of the above teachings. It is therefore to be understood that within the scope of the appended claims, the invention may be practiced otherwise than as specifically described herein.

When the terms "one", "a", or "an" are used in this document, they mean "at least one" or "one or more", unless otherwise indicated.

LIST OF DESIGNATIONS

1 Computer bridge interface
2 low-voltage frequency-adjustable electronic oscillator 3 signal generator
4 electronic switch
5 high voltage wide-band amplifier
6 analog to digital signal converter
7 card
8 analog to digital module
9 electronic memory
10 measuring device
11 casing
12 transducer
12' shear transducer
12" compression transducer
13 wave guide
13' first layer of wave guide
13" second layer of wave guide
14 coating
15 contacting material
16 joining material
17 temperature measuring element
18 means for taking up the material to be analyzed
19 temperature control element
20 apparatus
21 computer-readable medium
22 multiplexer unit
23 power supply
24 cable connection between transducer 12 and multiplexer unit 22
24' cable connection between temperature measuring element 17 and analog to digital module 8
24" cable connection between the temperature control elements 19
25 material to be analyzed
26 display unit
27 computer program product
28 multiplexer gate
29 data entry unit
30 switching unit
31 tension limiter
32 tension divider
33 transformer
33A first transformer
33B second transformer
33C third transformer
34 primary windings
35 secondary windings
36 power driver

The invention claimed is:

1. An apparatus for determining the dynamic elastic modulus of a sample of a material by means of sound waves, comprising
 (a) a measuring device with means for acoustically coupling the sample of the material to at least one transducer, which is coupled to
 (b) a card comprising
  (i) means for receiving and processing response signals received from the transducer and
  (ii) means for generating signals of a high voltage over a wide frequency range, said means including a low-voltage frequency-adjustable electronic oscillator, a signal generator, an electronic switch, and a high voltage wide-band amplifier, wherein said high voltage wide-band amplifier comprises or is connected to at least one coreless transformer having primary and secondary windings, wherein said secondary windings are connected to the at least one transducer.

2. The apparatus according to claim 1, wherein said at least one coreless transformer is a planar transformer.

3. The apparatus according to claim 1, wherein said high voltage wide-band amplifier comprises at least two coreless transformers, wherein the primary windings of the at least two coreless transformers are connected in parallel with one another and wherein the secondary windings of the at least two coreless transformers are connected in series.

4. The apparatus according to claim 1, wherein said frequency-adjustable oscillator is designed to generate at least $2^5$ discrete frequencies within the frequency range of 1 Hz to 200 MHz.

5. The apparatus according to claim 1, wherein said means for receiving and processing response signals received from the transducer comprise signal conditioning means such as a tension divider or a tension limiter, which signal conditioning means are connected to an analog to digital converter module which forwards digital response signals to a computer memory.

6. The apparatus according to claim 1, wherein computer means and a computer-readable medium are provided for controlling said means for receiving and processing response signals received from the transducer and/or for controlling said means for generating signals of high voltage.

7. The apparatus according to claim 1, with a multiplexer unit comprising m gates for transferring transmitted or received signals, m being the number of gates; with each gate being connected to a transducer $t_y$, wherein y is a varying index.

8. The apparatus according to claim 1, with a switching unit that is designed to transfer signals from the high voltage wide-band amplifier to the transducer, and to transfer signals from the transducer to the means for receiving and processing response signals.

9. The apparatus according to claim 1, wherein the means for acoustically coupling the sample of material to at least one transducer comprise at least one wave guide.

10. The apparatus according to claim 9, wherein said at least one wave guide is made of poly(methyl(meth)acrylate) or aluminum.

11. The apparatus according to claim 9, wherein said at least one wave guide is in contact with the at least one transducer by means of a contacting material, preferably a viscoelastic material.

12. The apparatus according to claim 9, wherein said at least one wave guide is at least partially covered by a coating such as a polymeric coating, preferably made on the basis of a polyurethane or epoxide resin.

13. The apparatus according to claim 9, wherein said wave guide comprises more than one layer of the same material or more than one layer of different materials, and wherein said layers are joint by a joining material, preferably an adhesive.

14. The apparatus according to claim 13, wherein said wave guide comprises a first and a second layer and wherein said first layer is of different material than said second layer and wherein said first layer is joint with said second layer by a joining material, preferably an adhesive.

15. The apparatus according to claim 1, wherein said at least one transducer is a shear transducer and/or a compression transducer.

16. The apparatus according to claim 1, wherein said at least one transducer is used as emitting and capturing transducer.

17. The apparatus according to claim 1, wherein said measuring device comprises at least two transducers, and wherein one transducer is used as emitting transducer and the other transducer is used as capturing transducer.

18. The apparatus according to claim 1, further comprising a temperature measuring element, preferably a thermocouple.

19. The apparatus according to claim 1, wherein said measuring device further comprises a means for receiving and holding the sample of material.

20. The apparatus according to claim 19, wherein said means is ring shaped.

21. The apparatus according to claim 19, wherein said means comprises a temperature control element.

22. The apparatus according to claim 1, wherein said material comprises a mineral binder or a polymer.

23. The apparatus of claim 22, wherein said mineral binder is a hydraulic binder such as cement or gypsum.

24. The apparatus of claim 22, wherein said material is mortar or concrete, in particular shotcrete.

25. A method for determining the dynamic elastic modulus of a sample of a material, said material comprising a polymer or mineral binder such as cement, or gypsum, by means of sound waves, with an apparatus according to claim 1, comprising the steps of
- (A) selecting a minimum frequency $f_{min}$ and a maximum frequency $f_{max}$, and a number of frequencies n;
- (B) sending data to a card for creating a first signal which is preferably transmitted to a multiplexer unit comprising m gates, m being the number of gates;
- (C) preferably selecting a gate $g_y$ which is connected to a transducer $t_y$, wherein y is a varying index;
- (D) isolating a frequency $f_x$ from the range of $f_{min}$ to $f_{max}$, wherein x is a varying index;
- (E) transmitting the first signal into the measuring device, leading to propagate sound, preferably ultrasound energy into the wave guide;
- (F) receiving a second signal from the transducer originating from the sound, preferably the ultrasound energy being transmitted or reflected from the wave guide or the material to be analyzed;
- (G) saving said second signal for the corresponding frequency $f_x$;
- (H) analyzing said second signal to determine amplitude and phase of the received sound, preferably ultrasound energy;
- (I) evaluating the real time evolution of the amplitude and the phase evolution;
- (J) increasing the varying index x by 1 and repeating the steps (B) to (I) until x is equal to n, n being the number of frequencies selected in step (A);
- (K) preferably increasing the varying index y by 1 and repeating the steps (B) to (J) until y is equal to m, m being the number of gates;
- (M) comparing amplitudes, phases and evolutions of the second signals obtained from a measurement without the material to be analyzed to the amplitudes, phases and evolutions of the corresponding second signals obtained from a measurement wherein said measuring device is in contact with the material to be analyzed;
- (N) calculating the dynamic elastic modulus from the comparison made in step (M).

26. The method according to claim 25, with a step (L) performed between step (K) and step (N), within step (L) repeating steps (B) to (K), wherein said measuring device is in contact with a material to be analyzed.

27. The method according to claim 25, wherein steps (B) to (K) are performed in parallel with and without material to be analyzed.

28. The method according to claim 25, wherein said steps are controlled by a computer.

* * * * *